US006307064B1

(12) United States Patent
Wuts et al.

(10) Patent No.: US 6,307,064 B1
(45) Date of Patent: Oct. 23, 2001

(54) PROCESS TO PREPARE TAXOL

(75) Inventors: Peter G. M. Wuts, Kalamazoo; Robert C. Kelly, Augusta, both of MI (US)

(73) Assignee: Pharmacia & Upjohn Company, Kalamazoo, MI (US)

( * ) Notice: Subject to any disclaimer, the term of this patent is extended or adjusted under 35 U.S.C. 154(b) by 0 days.

(21) Appl. No.: 09/304,792

(22) Filed: May 4, 1999

Related U.S. Application Data

(62) Division of application No. 08/827,957, filed on Apr. 10, 1997, now Pat. No. 6,057,452

(60) Provisional application No. 60/016,840, filed on May 8, 1996.

(51) Int. Cl.[7] .................................................. C07D 305/14

(52) U.S. Cl. .................................................. 549/214

(58) Field of Search .................................................. 549/214

(56) References Cited

U.S. PATENT DOCUMENTS

| | | | |
|---|---|---|---|
| 4,814,470 | 3/1989 | Colin et al. | 514/449 |
| 4,857,653 | 8/1989 | Colin et al. | 549/511 |
| 4,924,011 | 5/1990 | Denis et al. | 549/510 |
| 4,924,012 | 5/1990 | Colin et al. | 549/510 |
| 4,942,184 | 7/1990 | Haugwitz et al. | 514/449 |
| 4,960,790 | 10/1990 | Stella et al. | 514/449 |
| 5,015,744 | 5/1991 | Holton | 549/510 |
| 5,227,400 | 7/1993 | Holton et al. | 514/444 |
| 5,248,796 | 9/1993 | Chen | 549/510 |

FOREIGN PATENT DOCUMENTS

| | | |
|---|---|---|
| WO94/29284 | 12/1994 | (FR) . |
| 06319588 | 11/1994 | (JP) . |
| WO93/03838 | 3/1993 | (WO) . |
| WO93/06079 | 4/1993 | (WO) . |
| WO 94/07876 * | 4/1994 | (WO) . |
| WO94/29288 | 12/1994 | (WO) . |
| WO95/20582 | 8/1995 | (WO) . |

OTHER PUBLICATIONS

Taxol, Science and Applications, CRC Press, 1995, Ed. M. Suffness. Chapter 6.

*Drugs Fut.*, 21, 95 (1996).

Deng Li, et al., *J. Org. Chem.*, 57, pp 4320–4323 (1992).

Chang, et al., *Chem. Int. Ed. Engl.*, 35, pp 451–3 (1996).

Honig, H., et al., *Tetrahedron*, 46, pp 3841–3850 (1990).

*Chemical & Engineering News*, 6, (Feb. 19, 1996).

* cited by examiner

*Primary Examiner*—Brenda Coleman

(74) *Attorney, Agent, or Firm*—Bruce Stein

(57) ABSTRACT

The present invention includes processes to prepare commercially important taxols (X)

(X)

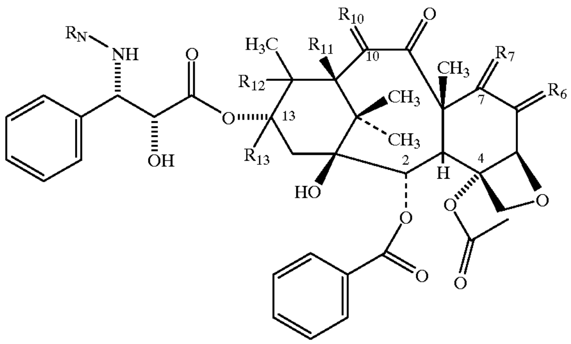

from substituted amino-3-phenyl (2R,3S) isoserinates (II). In addition processes to prepare the substituted amino-3-phenyl (2R,3S) isoserinates (II) as well as its precursor are set forth.

1 Claim, No Drawings

PROCESS TO PREPARE TAXOL

CROSS-REFERENCE TO RELATED APPLICATIONS

The present patent application is a divisional of U.S. patent application Ser. No. 08/827,957 filed Apr. 10, 1997 U.S. Pat. No. 6,037,452 which claims the benefit of U.S. provisional application Serial No. 60/016,840 filed May 8, 1996, under 35 USC §119(e)(i).

BACKGROUND OF THE INVENTION

1. Field of the Invention

The present invention is a chemical process to prepare taxol and taxol analogs by use of an arylsulfonyloxazolidine.

2. Description of the Related Art

Taxol and taxotere are known to be useful for treating cancer. Numerous documents disclose various processes to prepare taxol, taxotere and taxol analogs, see for example, "Taxol, Science and Applications", CRC Press, 1995, Ed. M. Suffness and *Drug Fut*., 21, 95 (1966).

International publication WO95/20582 discloses $\Delta^{6,12}$-taxol where the benzyl moiety on the side chain nitrogen has been replaced with $(CH_3)_3C$—NH—CO—, see EXAMPLE 32. In addition, various silyl protecting groups at C-7 were disclosed. These taxol derivatives were made by coupling an oxazolidine and an appropriately protected baccatin III moiety. The oxazolidine that was coupled was not a arylsulfonyloxazolidine.

International Publication WO93/06079 disclose a process to prepare compounds similar to the substituted amino-3-phenyl (2R,3S) isoserinates (II) by use of a β-lactam and not from a compound similar to the alkyl (2R,3S)-phenylisoserinates (I). There is no disclosure of any of the "$X_3$—" substituents of the present invention.

Japanese publication 06319588 discloses compounds similar to the nitriles (CCIII) of the present invention where $X_3$ of the present invention is hydrogen. In the present invention $X_3$ can not be hydrogen.

International Publication WO94/29284 discloses 2,2-dimethyl-4-(4-iodophenyl)oxazolidines which have traditional carbon/oxygen/hydrogen substituents attached to the 3-nitrogen. The oxazolidines of the present invention do not have any halogen on the 4-phenyl group and has sulfur containing substituents on the oxazolidine nitrogen.

U.S. Pat. No. 4,814,470 discloses taxol derivatives in which the isoserine side chain is different than that of the final products of the present invention. In addition, the process used to make these compounds is different than that of the present invention.

U.S. Pat. No. 4,857,653 discloses a process to produce taxol and 10-desacetyltaxol. The prior art process requires zinc and acid or fluoride to remove the $C_7$ protecting group. The $C_7$ silyl protecting groups of the present invention do not need zinc and acid to be removed. In addition, the isoserine side chain is produced by removal of a protecting group (BOC) whereas in the present invention the opening of an oxazolidine ring produces the isoserine side chain.

U.S. Pat. No. 4,924,011 discloses a process for coupling a hydroxy protected (2R,3S) 3-phenylisoserine derivative with a baccatin III or 10-deacetylbaccatin III to produce a taxol like compound. The present invention couples an oxazolidine, not a hydroxy protected (2R,3S)-3-phenylisoserine derivative to form a taxol precursor.

U.S. Pat. No. 4,924,012 discloses a process to prepare derivatives of baccatin III and of 10-desacetyl baccatin III which comprises coupling an isoserine-acid with a baccatin III-derivative. The present invention does not utilize an uncyclized isoserine-acid but rather an oxazolidine-acid.

U.S. Pat. No. 4,942,184 discloses water soluble taxol derivatives which do not contain a free hydroxyl group on the isoserine side chain. The compounds of the present invention have a free hydroxyl group on the isoserine side chain.

U.S. Pat. No. 4,960,790 discloses taxane compounds where either the hydroxyl group on the isoserine side chain or at $C_7$ is protected (with an amino acid). The present invention does not use any amino acid protecting groups.

U.S. Pat. No. 5,015,744 discloses a process for producing taxol using an oxazinone which is a six member ring. The process of the present invention uses a five member oxazolidine ring which is structurally and behaves mechanistically different from the oxazinone ring.

U.S. Pat. No. 5,227,400 discloses furyl and thienyl substituted taxanes which are produced from β-lactams and not by the processes of the present invention.

U.S. Pat. No. 5,248,796 discloses 10-desacetoxy-taxanes. The taxane products of the present invention have either an acetate or hydroxy function at $C_{10}$ in the β-configuration.

*J. Org. Chem*., 57, 4320–23 (1992) discloses the amminolysis of a phenyl substituted-epoxide-CO—O—$C_2H_5$ with ethanolic ammonia in a Parr reactor at 100°. The ammonolysis of the epoxide (CVI) uses aqueous ammonia and can be performed at room temperature.

International Publication WO95/20582 discloses a method for the preparation of taxol-like compounds which comprises coupling a oxazolidine and a baccatin III-type moiety. The oxazolidine which is coupled dose not contain a sulfonamide substituent.

*Chem. Int. Ed. Engl*., 35, 451–3 (1966) and *Chemical & Engineering News*, 6 (Feb. 19, 1996) discloses an osmium catalytized process to add amino and hydroxyl groups to carbon-carbon double bonds so that only one of two possible enantiomers is formed. This process can be used to produce β-hydroxyamino groups with specific chiralities. With regard to taxol, this document discloses the reaction sequence of methyl cinnamate being reacted according to the disclosed chemistry to produce a hydroxysulfonamide of phenylisoserine which is φ-CH(NHR)—CH(OH)—CO—$OCH_3$ where R is $CH_3$-φ-$SO_2$—. The toluenesulfonamide group is then removed to produce enantiomerically pure (2R,3S)phenylisoserine which is then reacted with φCO—Cl to produce the side chain required for taxol with >99% enantiomeric purity. The claimed invention does not use the sulfonamide as an intermediate for producing the taxol side chain but rather in producing an oxazolidine (not produced by the prior art) which is attached to the baccatin III portion of taxol prior to the opening of the oxazolidine.

Japanese publication JP06319588 discloses a 3(S)- and 3(R)-3(substituted)amino-2-hydroxynitriles, R(RNH)CH—CH(OH)—CN, where the substitution on the amino group does not include sulfur (—$SO_2$—) as in the present invention.

PCT patent application PCT/US95?00551 (International Publication WO95/20582) discloses a $\Delta^{12}$-taxol where the 3'-amino group is substituted with a 4-methylphenyl-$SO_2$—group. Unlike the 4-methylphenylsulfonamide group which is part of the active end product, the sulfonamide groups of the present invention are protecting groups and are lost prior to the formation of the final taxol (X) compound.

Oxazolidines are well known to those skilled in the art and are final end products with regard to some utilities and intermediates with regard to others. However, N-sulfonyl oxazolidines are not known.

SUMMARY OF INVENTION

Disclosed is a substituted amino-3-phenyl (2R,3S) isoserinate of formula (II)

$$\phi\text{—CH(NHX}_3\text{)—CH(OH)—CO—O—X}_1 \quad (II)$$

where $X_1$ is:

(1) $C_1$–$C_8$ alkyl, (2) $C_5$–$C_7$ cycloalkyl, (3) —$CH_2$-φ where the φ is optionally substituted with 1 or 2

(a) —O—$X_{1-1}$ where $X_{1-1}$ is $C_1$–$C_3$ alkyl, (b) —F, —Cl, —Br, —I;

where $X_3$ is —$SO_2$—$X_{31}$ where $X_{3-1}$ is:

(1) 4-nitrophenyl, (2) 2,4-dinitrophenyl.

Also disclosed is a substituted amino-3-phenyl (2R,3S) isoserinate of formula (II)

$$\phi\text{-CH(NHX}_3\text{)—CH(OH)—CO—O—X}_1 \quad (II)$$

where $X_1$ is:

(1) $C_1$–$C_8$ alkyl, (2) $C_5$–$C_7$ cycloalkyl, (3) —$CH_2$-φ where the φ is optionally substituted with 1 or 2

(a) —O—$X_{1-1}$ where $X_{1-1}$ is $C_1$–$C_3$ alkyl, (b) —F, —Cl, —Br, —I;

where $X_3$ is —$SO_2$—$X_{3-1}$ where $X_{3-1}$ is:

(1) 2-benzothiazol, (2) 9-anthracenyl, (3) 5-methyl-1,3,4-thiadiazolyl.

Further disclosed is an oxazolidine ester of formula (III) where $X_3$ is —$SO_2$—$X_{3-1}$ where $X_{3-1}$ is:

(1) 4-nitrophenyl, (2) 2,4-dinitrophenyl, (3) 2-benzothiazol, (4) 9-anthracenyl, (5) 5-methyl-1,3,4-thiadiazolyl and where $X_1$ is as defined above.

Additionally disclosed is an oxazolidine acid of formula (IV) where $X_3$ is —$SO_2$—$X_{3-1}$ where $X_{3-1}$ is:

(1) 4-nitrophenyl, (2) 2,4-dinitrophenyl, (3) 2-benzothiazol, (4) 9-anthracenyl, (5) 5-methyl-1,3,4-thiadiazolyl and where $X_2$ is as defined above and salts thereof.

Disclosed is an oxazolidine ester of silylated baccatin III of formula (VII) where $X_3$ is —$SO_2$—$X_{3-1}$ where $X_{3-1}$ is:

(1) 4-nitrophenyl, (2) 2,4-dinitrophenyl, (3) 2-benzothiazol, (4) 9-anthracenyl, (5) 5-methyl-1,3,4-thiadiazolyl;

where $R_6$ and $R_7$ are:

(1) $R_6$ is —H:—H and $R_7$ is α-H:β-$OR_{7-1}$ where $R_{7-1}$ is —$Si(R_{7-2})_3$ where $R_{7-2}$ is $C_1$–$C_5$ alkyl or $C_5$–$C_7$ cycloalkyl or mixtures thereof, and (2) $R_6$ is $R_{61}$:$R_{62}$ and $R_7$ is $R_{71}$:$R_{72}$ where one of $R_{61}$ and $R_{62}$ and one of $R_{71}$ and $R_{72}$ are taken together to form a second bond between the carbon atoms to which they are attached and the other of $R_{61}$ and $R_{62}$ is —H, and the other of $R_{71}$ and $R_{72}$ is —H;

where $R_{10}$ is:

(1) α-H:β-O—CO—$CH_3$ and (2) α-H:β-O—CO—O—$CH_2$—$CCl_3$;

where $R_{11}$, $R_{12}$ and $R_{13}$ are:

(1) $R_{11}$ and $R_{12}$ are taken together to form a second bond between the carbon atoms to which they are attached and $R_{13}$ is —H, (2) $R_{12}$ and $R_{13}$ are taken together to form a second bond between the carbon atoms to which they are attached and $R_{11}$ is —H and where $X_2$ is as defined above.

Also disclsoed is an oxazolidine of formula (XI) where $X_1$ is as defined above.

Further disclosed is an amino substituted phenylglycine of formula (CCII) where $X_3$ is:

(A) —$SO_2$—$X_{3-1}$ where $X_{3-1}$ is:

(1) 4-nitrophenyl, (2) 2,4-dinitrophenyl, (3) 2-benzothiazol, (4) 9-anthracenyl, (5) 5-methyl-1,3,4-thiadiazolyl, (B) —CO—$X_{3-2}$ where $X_{3-2}$ is:

(1) $C_1$–$C_8$ alkyl, (2) $C_1$–$C_8$ alkenyl containing 1 double bond, (3) -φ optionally substituted with 1 thru 3 substituents selected from the group consisting of:

(a) $C_1$–$C_4$ alkyl, (b) $C_1$–$C_3$ alkoxy, (c) —F, —Cl, —Br, —I, (d) $C_1$–$C_3$ alkylthio, (e) —$CF_3$, (f) $C_2$–$C_6$ dialkylamino, (g) —OH, (h) —$NO_2$, (4) 2- or 3-furyl, (5) 2- or 3-thienyl, (6) —$C(CH_3)$=$CHCH_3$, (C) —CO—O—$X_{3-3}$ where $X_{3-3}$ is:

(1) $C_1$–$C_8$ alkyl, (2) —$CH_2$(3)

(3)-4-tetrahydropyranyl, (D) —CO—NH—$X_{3-4}$ where $X_{3-4}$ is:

(1) $C_1$–$C_8$ alkyl, (2) -φ optionally substituted with 1 thru 3:

(a) $C_1$–$C_4$ alkyl, (b) $C_1$–$C_3$ alkoxy, (c) —F, —Cl, —Br, —I, (d) $C_1$–$C_3$ alkylthio, (e) —$CF_3$, (f) $C_2$–$C_6$ dialkylamino (g) —$NO_2$ where $X_1$ is as defined above.

Additionally disclosed is a nitrile of formula (CCIII) where $X_3$ is as defined above for the amino substituted phenylglycine of formula (CCII).

Disclosed is an imine of formula (CCIV) where $X_3$ is as defined above for the amino substituted phenylglycine of formula (CCII) and where $X_1$ is as defined above.

Also disclosed is a process for obtaining an enantiomerically pure (2S,3R)-2-chloro-3-hydroxypropionic acid which comprises:

(1) contacting a mixture of the four isomers of the formula $$\phi\text{-CH(OH)—CHCl—CO—O—X}_1$$

where $X_1$ is as defined above with an effective amount of a lipase at a temperature of from about 20 to about 40° in the presence of a buffer of pH about 6 to about 9 to produce (2S,3R)-2-chloro-3-hydroxypropionic acid and (2) separating the desired (2S,3R)-2-chloro-3-hydroxypropionic acid.

Further disclosed is a process for the preparation of the amide of formula (CVII) which comprises contacting a epoxide of formula (CVI) where $X_1$ is as defined above with aqueous ammonia at less than 70°.

Additionally disclosed is a phenylisoserine ester of silylated baccatin III (VIII) where $R_6$ and $R_7$ are (1) $R_6$ is —H:—H and $R_7$ is α-H:β-$OR_{7-1}$ where $R_{7-1}$ is —$Si(R_{7-2})_3$ where $R_{7-2}$ is $C_1$–$C_5$ alkyl or $C_5$–$C_7$ cycloalkyl or mixtures thereof, and where $R_{10}$ is (1) α-H:β-O—CO—$CH_3$ and (2) α-H:β-O—CO—O—$CH_2$—$CCl_3$; where $R_{11}$, $R_{12}$ and $R_{13}$ are (1) $R_{11}$ and $R_{12}$ are taken together to form a second bond between the carbon atoms to which they are attached and $R_{13}$ is —H.

DETAILED DESCRIPTION OF THE INVENTION

The first step of the process to produce taxol-like compounds is the conversion of alkyl (2R,3S)-phenylisoserinates (I) to the corresponding substituted amino-3-phenyl (2R,3S) isoserinates (II).

The alkyl (2R,3S)-phenylisoserinates (I) are known to those skilled in the art or can be readily prepared from known ketones (CI) by methods known to those skilled in the art, see CHART F. The substituted amino-3-phenyl (2R,3S) isoserinates (II) can be prepared from the alkyl (2R,3S)-phenylisoserinates (I) or from the phenylglycine compounds (CCI), see CHART G.

When it is desired to prepare the alkyl (2R,3S)-phenylisoserinates (I) rather than purchase them from commercial sources the starting material are the ketones (CI), φ-CO—CHCl—CO—O—$X_1$ which are known to those skilled in the art or can be readily prepared from known compounds by methods known to those skilled in the art, see *J. Org. Chem.*, 29, 2459 (1964). The process for preparation of the alkyl (2R,3S)phenylisoserinates (I) from the ketones (CI) is set forth in CHART F. $X_1$ is (1) $C_1$–$C_8$ alkyl, (2) $C_5$–$C_7$ cycloalkyl, (3) —$CH_2$-φ where the -φ is optionally substituted with 1 or 2

(a) —O—$X_{1-1}$ where $X_{1-1}$ is $C_1$–$C_3$ alkyl, (b) —F, —Cl, —Br, —I; it is preferred that $X_1$ is $C_1$, $C_2$ or $C_4$ as —$CH_2$—$CH(CH_3)_2$.

The ketone (CI) is transformed to the corresponding halohydrin (CII) by reduction as is known to those skilled in the art. Suitable reducing agents include sodium borohydride or zinc borohydride, sodium borohydride is preferred because it is easier to work with. The two borohydrides give different ratios of syn/anti isomers. The reduction is preferably performed in the presence of one equivalent of acid, preferably acetic acid. Sodium borohydride gives a ratio of about 4/1 syn/anti and zinc borohydride gives a ratio of about 9/1; the ratio is not important. Because of the two enantiomeric centers a racemic mixture of four isomers is produced.

The mixture of four halohydrin (CII) isomers is then subjected to enzymatic resolution with a lipase by methods known to those skilled in the art. It is preferred that the lipase be MAP-10. The lipase MAP-10 is preferred because of its syn/anti selectivity as well as its enantioselectivity. The four halohydrin (CII) isomeric esters when subjected to the MAP-10 lipase produce the desired β-halohydrin acid (CIV) and leaves the isomeric α-halohydrin ester (CIII) along with the other syn/anti halohydrin (CII) esters. Almost any amount of the lipase is effective, the more added the faster the reaction will be complete. It is preferred to preform the reaction at a temperature of from about 20 to about 40° in the presence of a buffer of pH about 6 to about 9. Simple acid/base extraction permits separation of the desired β-halohydrin acid (CIV) from the esters (CII) and (CIII).

The β-halohydrin acid (CIV) is then converted by known means to the corresponding ester, β-halohydrin ester (CV), preferably the methyl ester by use of methanol and acid, preferably gaseous hydrochloric acid.

The β-halohydrin ester (CV) is then transformed to the corresponding epoxide (CVI) by methods known to those skilled in the art, such as weak base in a polar solvents such as DMF, acetonitrile, pyridine; preferred is DMF. The epoxides (CVI) are known, see *J. Org. Chem.*, 55, 1957 (1990). Suitable bases include sodium and potassium carbonate, sodium and potassium bicarbonate, preferred is potassium carbonate in DMF. During the formation of the epoxide (CVI), the trans epoxide is selectively hydrolyzed in preference to the cis isomer. Thus any anti-β-halohydrin ester (CV) present during the ring closure is removed from the reaction because of its rapid hydrolysis relative to the cis epoxide (CVI).

The epoxide (CVI) is then transformed to the corresponding amide (CVII). The process of opening an epoxide with azide ion is known to those skilled in the art. While this reaction works well it is not suitable for commercial scale because the intermediate azido derivative is quite explosive. Also the process of opening an epoxide with ammonia is known, see *J. Org. Chem.*, 57, 4320–23 (1992) which discloses the amminolysis of a phenyl substituted-epoxide-CO—O—$C_2H_5$ with ethanolic ammonia in a Parr reactor at 100°. The ammonolysis of the present invention uses aqueous ammonia and can be performed at room temperature. If the amide (CVII) is to be crystallized from methanol, the racemic material will not dissolve while the optically pure will dissolve and recrystallize.

The amide (CVII) is converted to the corresponding alkyl (2R,3S)phenylisoserinate (I) by heating an isobutyl alcohol slurry of the amide to about 100° after saturating with hydrochloric acid gas, see *Angew. Chem. Int. Ed.*, 33, 2076 (1994). Neutralization of the ester salt gives the alkyl (2R,3S)phenylisoserinate (I). This enantiomerically pure alkyl (2R,3S)phenylisoserinate (I) is the starting material for the taxol side chain in the process of the invention.

CHART G discloses the process to transform the known phenylglycine compounds (CCI) to the corresponding substituted amino-3-phenyl (2R,3S) isoserinates (II). The phenylglycine compounds (CCI) are first reacted with the appropriate alkylating agent ($X_3$-halogen) by means well known to those skilled in the art to produce the corresponding amino substituted phenylglycine (CCII). It is preferred that halogen is chlorine. For the amino substituted phenylglycine compounds (CCII), $X_3$ includes:

(A) —$SO_2$—$X_{3-1}$ where $X_{3-1}$ is: (1) 4-nitrophenyl, (2) 2,4-dinitrophenyl, (3) 2-benzothiazol, (4) 9-anthracenyl, (5) 5-methyl-1,3,4-thiadiazolyl, (B) —CO—$X_{3-2}$ where $X_{3-2}$ is: (1) $C_1$–$C_8$ alkyl, (2) $C_1$–$C_8$ alkenyl containing 1 double bond, (3) -φ optionally substituted with 1 thru 3 substituents selected from the group consisting of: (a) $C_1$–$C_4$ alkyl, (b) $C_1$–$C_3$ alkoxy, (c) —F, —Cl, —Br, —I; (d) $C_1$–$C_3$ alkylthio, (e) —$CF_3$, (f) $C_2$–$C_6$ dialkylamino, (g) —OH, (h) —$NO_2$, (4) 2- or 3-furyl, (5) 2- or 3-thienyl, (6) —$C(CH_3)$═$CHCH_3$, (C) —CO—O—$X_{3-3}$ where $X_{3-3}$ is: (1) $C_1$–$C_8$ alkyl, (2) —$CH_2$-φ, (3) -4-tetrahydropyranyl, (D) —CO—NH—$X_{3-4}$ where X3-4 is: (1) $C_1$–$C_8$alkyl, (2) -φ optionally substituted with 1 thru 3: (a) $C_1$–$C_4$ alkyl, (b) $C_1$–$C_3$ alkoxy, (c) —F, —Cl, —Br, —I, (d) $C_1$–$C_3$ alkylthio, (e) —$CF_3$, (f) $C_2$–$C_6$ dialkylamino and (g) —$NO_2$. It is preferred that $X_3$ is —$SO_2$—$X_{3-1}$ or —CO—$X_{3-2}$; it is more preferred that $X_3$ is —$SO_2$—$X_{3-1}$.

The amino substituted phenylglycine (CCII) is then transformed to the corresponding nitrile (CCIII) by dissolving the amino substituted phenylglycine (CCII) in an inert solvent (preferably THF) under an inert atmosphere (nitrogen) and cooled to about −78°. This mixture is then contacted with a reducing agents such as diisobutyl aluminum hydride. The reaction mixture can be warmed to about −60 to about −70°. Cyanide, peferably as potassium cyanide, is then added followed by an alcohol, preferably methanol and a weak acid preferably acetic acid. When the nitrile (CCIII) is produced it is not diastereomerically pure. The amino substituent at the 3'-position is (S) however the hydroxyl substituent at the 2'-position is both (S) and (R). Therefore a mixture of (3S,2S)- and (3S,2R)- are produced. While it is important that the attachment between the oxazolidine portion and the baccatin III portion of the oxazolidine silylated baccatin III (VII) be have the correct (2'R) configureation that is not a problem because regardless of whether the 7-silylated-10-acylated baccatin III (VI) is coupled with a (3S,2S) and (3S,2R)-oxazolidine acid (IV), the resulting product the oxazolidine silylated baccatin III (VII) will have the correct stereochemistry at the 2'-position. Therefore, not only is it not necessary or desirable to separate the (3S,2S)- and (3S,2R)-nitriles (CCIII), it is counterproductive. The mixture is carried on thru the entire reaction sequence as a mixture and reacted as such all the way to the reaction of the (3S,2S) and (3S,2R)-oxazolidine acid (IV) with the 7-silylated-10-acylated baccatin III (VI) to give only the desired (3S,2R)-oxazolidine silylated baccatin III (VII). Because of this, when any of the terms substituted amino-3-phenyl (2R,3S) isoserinate (II), oxazolidine ester (III) and/or oxazolidine acid (IV) are used in this patent they are meant to specify the enantiomerically pure form if produced by the process of CHART F and the diastereomerically impure form if produced by the process of CHART G. Regardless of the diastereomeric purity (and process produced by) they are all useful in producing the oxazolidine silylated baccatin III (VII).

The nitrile (CCIII) is then transformed to the corresponding imine (CCIV) and then to the corresponding substituted amino-3-phenyl (2R,3S)/(2S,3S) isoserinate (II) all in one pot. The nitrile (CCIII) is dissolved in a suitable solvent such as methanol, ethanol, etc and an acid is added. The nature of the acid is not critical, a strong acid is preferred. If methanol is the solvent, the substituted amino-3-phenyl (2R,3S) isoserinate (II) formed will be the methyl ester. Similarly, if ethanol is the solvent, the substituted amino-3-phenyl (2R, 3S) isoserinate (II) formed will be the ethyl ester.

Because of the stereochemistry at the two enantiomeric centers in the side chain of the taxol (X) products, it is necessary that the alkyl phenylisoserinate (I) starting material have the (3S) configuration. It is also important that the alkyl (2R,3S)-phenylisoserinate (I) be an ester, —CO—$OX_1$. However, the particular ester used (the particular —$X_1$ group) is not important. It is preferred that $X_1$ be methyl, ethyl or i-butyl.

The alkyl (2R,3S)-phenylisoserinate (I) starting material is transformed to the corresponding substituted amino-3-phenyl (2R,3S) isoserinate (II) by one of two basic processes. The first process involves disolving the alkyl (2R, 3S)-phenylisoserinate (I) in a basic amine solvent, such as pyridine, or a basic amine solvent and an inert solvent, such as methylene chloride. It is preferred that the basic amine solvent be pyridine and the inert solvent be methylene chloride. Then the appropriate arylsulfonylhalide ($X_3$-halide) is added. $X_3$ includes —$SO_2$—$X_{3-1}$ where $X_{3-1}$ is: (1) 4-nitrophenyl, (2) 2,4-dinitrophenyl, (3) 2-benzothiazol, (4) 9-anthracenyl and (5) 5-methyl-1,3,4-thiadiazolyl. For the amino-3-phenyl (2R,3S) isoserinate (II), the oxazolidine ester (III), oxazolidine acid (IV) and oxazolidine silylated baccatin III (VII) it is preferred that $X_3$ is 4-nitrophenyl and 2,4-dinitrophenyl. It is also preferred that $X_3$ is 2-benzothiazol, 9-anthracenyl and 5-methyl-1,3,4-thiadiazolyl. It is preferred that halide be —Cl. Since only primary amines are involved, the reaction temperature is not critical; it usuually is about 0° to about 25°.

The substituted amino-3-phenyl (2R,3S) isoserinates (II) thus prepared may be isolated either by precipitation with water or by extraction with a suitable solvent.

The other method for the transformation of the alkyl (2R,3S)-phenylisoserinates (I) to the corresponding substituted amino-3-phenyl (2R,3S) isoserinate (II) is by use of the Schotten-Bauman reaction. Following this proceedure the alkyl (2R,3S)-phenylisoserinate (I) is dissolved or slurried in water or water containing a cosolvent such as tetrahydrofuran, treated with a weak base such as sodium bicarbonate or potassium carbonate followed by the addition of the arylsulfonylhalide. When the reaction is complete the substituted amino-3-phenyl (2R,3S) isoserinates (II) can be isolated by means known to those skilled in the art, preferably by direct filtration or isolation with a suitable solvent.

The substituted amino-3-phenyl (2R,3S) isoserinates (II) are transformed to the corresponding oxazolidine esters (III) by contacting the appropriate substituted amino-3-phenyl (2R,3S) isoserinate (II) in a solvent capable of forming a water azeotrope with an aromatic aldehyde and an acid. It is known to those skilled in the art that azeotropic removal of water at reflux results in formation of the oxazolidine esters (E). Suitable solvents capable of forming a water azeotrope include toluene, heptane, benzene and mixtures thereof; preferred is toluene. Suitable aromatic aldehydes include benzaldehyde, anisaldehyde, dimethoxybenzaldehyde, preferred is benzaldehyde. Operable acids include p-toluenesulfonic, pyridinium toluenesulfonate, pyridinium hydrochloride. The stereochemistry of the product produced depends on the $pK_a$ of the acid used. Weak acids such as pyridinium hydrochloride give the kinetic product and strong acids such as p-toluenesulfonic give the thermodynamic product. The kinetic and thermodynamic products are controlled by the nature of the "$X_3$—" substituent. It is not critical whether the oxazolidine ester (III) produced be the (2R)- or the (2S)- since both give the same product when the oxazolidine ring is opened. The difference between the two will affect the speed of the cleavage reaction during deprotection. The use of an aryldimethylacetal and acid with distillative removal of methanol also gives the oxazolidine esters (III), see for example *Tetrahedron Lett.*, 35, 2349 (1994).

The transformation of oxazolidine esters (III) to the corresponding oxazolidine acids (IV) is very well known to those skilled in the art. The oxazolidine esters (III) are reacted in aqueous alcoholic solvent with a base such as potassium carbonate or sodium hydroxide to form the salt.

Acidification and isolation with a suitable solvent gives the acid. Since the salts are converted to the acid, for purposes of this invention the salts of the oxazolidine acids (IV) are considered equivalent to the oxazolidine acids (IV). The nature of the particular salt is unimportant and virtually all bases/salts will be operate in producing the desired oxazolidine acids (IV).

The 10-desacetylbaccatin III (V), also known as 10DAB, is transformed to the corresponding 7-silylated-10-acylated baccatin III (VI) by means known to those skilled in the art before it is attached to the phenylisoserinate side chain. The reason is that even though a free hydroxyl group is desired at $C_7$ in taxol and taxotere, it is the most reactive of the hydroxyl groups and so prior to coupling at $C_{13}$ it must be protected. The acetate group at $C_{10}$ is part of the final product in taxol and 13-(N-t-butylaminocarbonyl)-β-phenylisoserinyl)-7-deoxy-$\Delta^{6,12}$-iso-baccatin III. For taxotere a removable protecting group (—O—CO—O—$CH_2$—$CCl_3$ or —CO—$CH_3$) is used at $C_{10}$ because the final product requires a free hydroxyl group at $C_{10}$. When the removable protecting group is acetate, it is removed as set forth in *Tetrahedron Lett*., 35, 7893 (1944). With regard to the 10DAB (V), the substituents at $C_6$, $C_7$, $C_{10}$, $C_{11}$, $C_{12}$ and $C_{13}$ will vary depending on the particular taxol (X) product desired.

With regard to $C_6$ and $C_7$, $R_6$ and $R_7$ are:

(1) $R_6$ is —H:—H and $R_7$ is α-H:β-$OR_{7-1}$ where $R_{7-1}$ is —$Si(R_{7-2})_3$ where $R_{7-2}$ is $C_1$–$C_5$ alkyl or $C_5$–$C_7$ cycloalkyl or mixtures thereof, and (2) $R_6$ is $R_{61}$:$R_{62}$ and $R_7$ is $R_{71}$:$R_{72}$ where one of $R_{61}$ and $R_{62}$ and one of $R_{71}$ and $R_{72}$ are taken together to form a second bond between the carbon atoms to which they are attached and the other of $R_{61}$ and $R_{62}$ is —H, and the other of $R_{71}$ and $R_{72}$ is —H. $R_{10}$ is: (1) α—H:β-O—CO—$CH_3$ and (2) α-H:β-O—CO—O—$CH_2$—$CCl_3$. $R_{11}$, $R_{12}$ and $R_{13}$ are:

(1) $R_{11}$ and $R_{12}$ are taken together to form a second bond between the carbon atoms to which they are attached and $R_{13}$ is —H, (2) $R_{12}$ and $R_{13}$ are taken together to form a second bond between the carbon atoms to which they are attached and $R_{11}$ is —H. These variable substituents provide for and include the baccatin III portion of three important taxol-type compounds. It is preferred that $R_{7-1}$ is selected from the group consisting of —Si[$C_1$ alkyl]$_2$[—CH($CH_3$)—CH$(CH_3)_2$], —Si[$C_1$ alkyl]$_2$[cyclohexyl], —Si[$C_1$ alkyl]$_2$[cycloheptyl] and —Si[$C_1$ alkyl]$_2$[$C_4$ alkyl]; it is more preferred that $R_{7-1}$ is —Si[$C_1$ alkyl]$_2$[—CH($CH_3$)—CH$(CH_3)_2$].

To produce taxol (X) it is necessary that in the 7-silylated-10-acylated baccatin III (VI) $R_6$ is —H:—H and $R_7$ is α-H:β-$OR_{7-1}$ where $R_{7-1}$ is —$Si(R_{7-2})_3$ where $R_{7-2}$ is $C_1$–$C_5$ alkyl or $C_5$–$C_7$ cycloalkyl or mixtures thereof; that $R_{10}$ is α-H:β-O—CO—$CH_3$, $R_{11}$ and $R_{12}$ are taken together to form a second bond between the carbon atoms to which they are attached and $R_{13}$ is —H.

To produce taxotere it is necessary that in the 7-silylated-10-acylated baccatin III (VI) $R_6$ is —H:—H and $R_7$ is α-H:β-$OR_{7-1}$ where $R_{7-1}$ is —$Si(R_{7-2})_3$ where $R_{7-2}$ is $C_1$–$C_5$ alkyl or $C_5$–$C_7$ cycloalkyl or mixtures thereof; that $R_{10}$ is α-H:β-O—CO—O—$CH_2$—$CCl_3$ or —CO—$CH_3$, $R_{11}$ and $R_{12}$ are taken together to form a second bond between the carbon atoms to which they are attached and $R_{13}$ is —H.

To produce 13-(N-(t-butylaminocarbonyl)-β-phenylisoserinyl)-7-deoxy-$\Delta^{6,12}$-iso-baccatin III, it is necessary that in the 7-silylated-10-acylated baccatin III (VI) $R_6$ is $R_{61}$:$R_{62}$ and $R_7$ is $R_{71}$:$R_{72}$ where one of $R_{61}$ and $R_{62}$ and one of $R_{71}$ and $R_{72}$ are taken together to form a second bond between the carbon atoms to which they are attached and the other of $R_{61}$ and $R_{62}$ is —H, and the other of $R_{71}$ and $R_{72}$ is —H, that $R_{10}$ is α-H:β-O—CO—$CH_3$, $R_{12}$ and $R_{13}$ are taken together to form a second bond between the carbon atoms to which they are attached and $R_{11}$ is —H. The silylation and esterification of alcohols is well know to those skilled in the art and is extensively described in "Protective Groups in Organic Synthesis", T. W. Green and P. G. M. Wuts, Wiley, 1991. More particularly, numerous documents have disclosed the protection (silylation) and acylation of the $C_7$ and/or $C_{10}$ positions of 10DAB, see for example, *J. Am. Chem. Soc*., 110, 5917 (1988).

The coupling (esterification) of the oxazolidine acids (IV) with the 7-silylated-10-acylated baccatin III (VI) to produce the corresponding oxazolidine silylated baccatin III (VII) can be performed by a number of methods known to those skilled in the art. The preferred method is to use a coupling agent such as dicyclohexylcarbodiimide (DCC) in an inert solvent such as toluene with a catalytic amount of dimethylaminopyridine, see for example, *Tetrahedron Lett*., 35, 2349 (1994).

The deprotection of the oxazolidine silylated baccatin III (VII) to produce the corresponding phenylisoserine ester of silylated baccatin III (VIII) is performed by means known to those skilled in the art. It is known that 4-nitrosulfonamides and acylated anthracenesulfonamides can be cleaved using thiolate, see *Tetrahedron Lett*., 36, 6373 (1995) and *Science*, 269, 202 (1995) respectively. Thiolate also works for the benzthiazolesulfonamides and the alkyl substituted anthracenesulfonamides. The deprotection reaction is performed by reacting the sulfonamide, the oxazolidine silylated baccatin III (VII), in an aprotic dipolar solvent such as DMF or in combination with another solvent such as THF with a thiolate generated from a thiol and a base. Suitable bases to generate the thiolate include Hunigs base and potassium t-butoxide. When the reaction is complete, the reaction mixture is treated with acid to remove the aldehyde from the amino alcohol before isolation with a suitable solvent. The aldehyde may also be removed by trapping with sodium bisulfite.

The phenylisoserine ester of silylated baccatin III (VIII) is then N-acylated to produce the corresponding N-substituted isoserine silylated baccatin III (IX) by methods well known to those skilled in the art, see for example, "Protective Groups in Organic Synthesis", T. W. Green and P. G. M. Wuts, Wiley, 1991 where many methods to effect this transformation are disclosed. More particularly, with regard to acylation of $C_{10}$ of taxol type compounds, see *Tetrahedron Lett*., 36, 1985 (1995). It is preferred that $R_N$ is (1) ϕ-CO—, (2) $(CH_3)_3C$—NH—CO— and (3) $(CH_3)_3C$—O—CO—; it is more preferred that $R_N$ is (1) ϕ-CO—. The acylation of the phenylisoserine ester of silylated baccatin III (VIII) to produce the corresponding N-substituted isoserine silylated baccatin III (IX) can be performed before or after the removal of the silyl protecting group at $C_7$.

The N-substituted isoserine silylated baccatin III (IX) is then desilylated to produce the corresponding taxol (X) by methods well known to those skilled in the art, see for example, "Protective Groups in Organic Synthesis", T. W. Green and P. G. M. Wuts, Wiley, 1991. More particularly, with regard to taxol-type compounds, see *J. Am. Chem. Soc*., 110, 5917 (1988). For taxotere, following removal of the silyl group at $C_7$, the protecting group —CO—O—$CH_2$—$CCl_3$ at $C_{10}$ is removed by zinc in acetic acid to produce the free hydroxyl group which is required in taxotere.

For the important taxol compounds, taxol, taxotere and 13-(N-(t-butylaminocarbonyl)-β-phenylisoserinyl)-7-deox-$\Delta^{6,12}$-iso-baccatin III, the substitution of the side chain and on the baccatin III ring system is as follows, for (1) taxol $R_N$ is φ-CO— and $R_6$ is —H:—H, $R_7$ is α-H:β-OH, $R_{10}$ is α-H:β-O—CO—$CH_3$ and $R_{11}$ and $R_{12}$ are taken together to form a second bond between the carbon atoms to which they are attached and $R_{13}$ is —H; for (2) taxotere $R_N$ is $(CH_3)_3$C—O—CO— and $R_6$ is —H:—H, $R_7$ is α-H:β-OH, $R_{10}$ is α-H:β-OH and $R_{11}$ and $R_{12}$ are taken together to form a second bond between the carbon atoms to which they are attached and $R_{13}$ is —H; and for (3) 13-(N-(t-butylaminocarbonyl)-β-phenylisoserinyl)-7-deoxy-$\Delta^{6,12}$-iso-baccatin III, $R_N$ is $(CH_3)_3$C—NH—CO— and $R_6$ is $R_{61}$:$R_{62}$ and $R_7$ is $R_{71}$:$R_{72}$ where one of $R_{61}$ and $R_{62}$ and one of $R_{71}$ and $R_{72}$ are taken together to form a second bond between the carbon atoms to which they are attached and the other of $R_{61}$ and $R_{62}$ is —H, and the other of $R_{71}$ and $R_{72}$ is —H, $R_{10}$ is α-H:β-O—CO—$CH_3$ and $R_{12}$ and $R_{13}$ are taken together to form a second bond between the carbon atoms to which they are attached and $R_{11}$ is —H.

While there are process routes of protecting/deprotecting before/after other process steps are preformed, for taxol, taxotere and 13-(N-(t-butylaminocarbonyl)-β-phenylisoserinyl)-7-deoxy-$\Delta^{6,12}$-iso-baccatin III the following order of process steps is preferred. For taxol, when the phenylisoserine ester of silylated baccatin III (VIII) is acylated to produce the N-substituted isoserine silylated baccatin III (IX), it is desired that $R_N$ is φ-CO—; $R_6$ is —H:—H; $R_7$ is α-H:β-$OR_{7-1}$ where $R_{7-1}$ is —Si$(R_{7-2})_3$ where $R_{7-2}$ is $C_1$–$C_5$ alkyl or $C_5$–$C_7$ cycloalkyl or mixtures thereof; $R_{10}$ is α-H:β-O—CO—$CH_3$; $R_{11}$ and $R_{12}$ are taken together to form a second bond between the carbon atoms to which they are attached and $R_{13}$ is —H. It is preferred that $R_{71}$ is siamyldimethylsilyl (SDMS). When the N-substituted isoserine silylated baccatin III (IX) is transformed to the taxol (X) the silyl protecting group at $C_7$ is removed by methods known to those skilled in the art resulting in the formation of taxol (X) itself.

For taxotere, when the phenylisoserine ester of silylated baccatin III (VIII) is acylated to produce the N-substituted isoserine silylated baccatin III (IX), it is desired that $R_N$ is $(CH_3)_3$C—O—CO—; $R_6$ is —H:—H; $R_7$ is α-H:β-$OR_{7-1}$ where $R_{7-1}$ is —Si$(R_{7-2})_3$ where $R_{7-2}$ is $C_1$–$C_5$ alkyl or $C_5$–$C_7$ cycloalkyl or mixtures thereof; $R_{10}$ is α-H:β-O—CO—O—$CH_2$—$CCl_3$; $R_{11}$ and $R_{12}$ are taken together to form a second bond between the carbon atoms to which they are attached and $R_{13}$ is —H. It is preferred that $R_{7-1}$ is siamyldimethylsilyl (SDMS). When the N-substituted isoserine silylated baccatin III (IX) is transformed to the taxol (X) generically but specifically taxotere, the silyl protecting group at $C_7$ and the protecting group at $C_{10}$ are removed by methods known to those skilled in the art resulting in the formation of taxotere (X) itself. The silyl group at $C_7$ is removed first followed by the protecting group at $C_{10}$ using zinc in acetic acid to produce the free hydroxyl group at $C_{10}$ required in taxotere.

For 13-(N-(t-butylaminocarbonyl)-β-phenylisoserinyl)-7-deoxy-$\Delta^{6,12}$-iso-baccatin III, it is desired that both the $\Delta^6$- and $\Delta^{12}$-double bonds be present early in the synthesis, preferably at the stage of the protection of 10-desacetylbaccatin III (V) to the corresponding 7-silylated-10-acylated baccatin III (VI). Therefore, when the phenylisoserine ester of silylated baccatin III (VIII) is acylated to produce the N-substituted isoserine silylated baccatin III (IX), it is desired that $R_N$ is $(CH_3)_3$C—NH-CO—; $R_6$ is $R_{61}$:$R_{62}$ and $R_7$ is $R_{71}$:$R_{72}$ where one of $R_{61}$ and $R_{62}$ and one of $R_{71}$ and $R_{72}$ are taken together to form a second bond between the carbon atoms to which they are attached and the other of $R_{61}$ and $R_{62}$ is —H, and the other of $R_{71}$ and $R_{72}$ is —H; $R_{10}$ is α-H:β-O—CO—$CH_3$; $R_{11}$ is —H; $R_{12}$ and $R_{13}$ are taken together to form a second bond between the carbon atoms to which they are attached. With regard to 13-(N-(t-butylaminocarbonyl)-β-phenylisoserinyl)-7-deoxy-$\Delta^{6,12}$-iso-baccatin III (X), when the N-substituted isoserine silylated baccatin III (IX) is produced the final product is also produced since there is no need for deprotection.

An alternative way to prepare the oxazolidine ester (III) from the alkyl (2R,3S)-phenylisoserinate (I) is by use of formaldehyde or an aldehyde which must have sufficient electron withdrawing groups, such as trichloroacetaldehyde and a solvent such as THF. The usual way of transforming amino alcohols such as the alkyl (2R,3S)-phenylisoserinate (I) to oxazolidines such as the oxazolidine ester (III) is by use of an aldehyde having powerful electron withdrawing groups. Normally, if aldehydes such as benzaldehyde are used which do not have sufficient electron withdrawing groups, the product of O-sulfonylation is obtained because it forms an imine rather than an oxazolidine.

Both taxol and taxotere have been approved by the US Federal Food and Drug Administration (FDA) for treating humans with cancer. Other analogs such as 13-(N-(t-butylaminocarbonyl)-β-phenylisoserinyl)-7-deoxy-$\Delta^{6,12}$-iso-baccatin III are useful in treating cancer, see International publication WO95/20582.

DEFINITIONS AND CONVENTIONS

The definitions and explanations below are for the terms as used throughout this entire document including both the specification and the claims.

I. CONVENTIONS FOR FORMULAS AND DEFINITIONS OF VARIABLES

The chemical formulas representing various compounds or molecular fragments in the specification and claims may contain variable substituents in addition to expressly defined structural features. These variable substituents are identified by a letter or a letter followed by a numerical subscript, for example, "$Z_1$" or "$R_i$" where "i" is an integer. These variable substituents are either monovalent or bivalent, that is, they represent a group attached to the formula by one or two chemical bonds. For example, a group $Z_1$ would represent a bivalent variable if attached to the formula $CH_3$—C(=$Z_1$)H. Groups $R_i$ and $R_j$ would represent monovalent variable substituents if attached to the formula $CH_3$—$CH_2$—C($R_i$)($R_j$)—H. When chemical formulas are drawn in a linear fashion, such as those above, variable substituents contained in parentheses are bonded to the atom immediately to the left of the variable substituent enclosed in parenthesis. When two or more consecutive variable substituents are enclosed in parentheses, each of the consecutive variable substituents is bonded to the immediately preceding atom to the left which is not enclosed in parentheses. Thus, in the formula above, both $R_i$ and $R_j$ are bonded to the preceding carbon atom. Also, for any molecule with an established system of carbon atom numbering, such as steroids, these carbon atoms are designated as $C_i$, where "i" is the integer corresponding to the carbon atom number. For example, $C_6$ represents the 6 position or carbon atom number in the steroid nucleus as traditionally designated by those skilled in the art of steroid chemistry. Likewise the term "$R_6$" represents a variable substituent (either monovalent or bivalent) at the $C_6$ position.

Chemical formulas or portions thereof drawn in a linear fashion represent atoms in a linear chain. The symbol "—" in general represents a bond between two atoms in the chain. Thus $CH_3$—O—$CH_2$—CH($R_i$)—$CH_3$ represents a 2-substituted-1 methoxypropane compound. In a similar fashion, the symbol "═" represents a double bond, e.g., $CH_2$═C($R_i$)—O—$CH_3$, and the symbol "≡" represents a triple bond, e.g., HC≡C—CH($R_i$)—$CH_2$—$CH_3$. Carbonyl groups are represented in either one of two ways: —CO— or —C(═O)—, with the former being preferred for simplicity.

Chemical formulas of cyclic (ring) compounds or molecular fragments can be represented in a linear fashion. Thus, the compound 4 chloro-2-methylpyridine can be represented in linear fashion by N*═C($CH_3$)—CH═CCl—CH═C*H with the convention that the atoms marked with an asterisk (*) are bonded to each other resulting in the formation of a ring. Likewise, the cyclic molecular fragment, 4-(ethyl)-1-piperazinyl can be represented by —N*—$(CH_2)_2$—N($C_2H_5$)—$CH_2$—C*$H_2$.

A rigid cyclic (ring) structure for any compounds herein defines an orientation with respect to the plane of the ring for substituents attached to each carbon atom of the rigid cyclic compound. For saturated compounds which have two substituents attached to a carbon atom which is part of a cyclic system, —C($X_1$)($X_2$)— the two substituents may be in either an axial or equatorial position relative to the ring and may change between axial/equatorial. However, the position of the two substituents relative to the ring and each other remains fixed. While either substituent at times may lie in the plane of the ring (equatorial) rather than above or below the plane (axial), one substituent is always above the other. In chemical structural formulas depicting such compounds, a substituent ($X_1$) which is "below" another substituent ($X_2$) will be identified as being in the alpha (α) configuration and is identified by a broken, dashed or dotted line attachment to the carbon atom, i.e., by the symbol " - - - " or " . . . ". The corresponding substituent attached "above" ($X_2$) the other ($X_1$) is identified as being in the beta (β) configuration and is indicated by an unbroken line attachment to the carbon atom.

When a variable substituent is bivalent, the valences may be taken together or separately or both in the definition of the variable. For example, a variable $R_i$ attached to a carbon atom as —C(═$R_i$)— might be bivalent and be defined as oxo or keto (thus forming a carbonyl group (—CO—) or as two separately attached monovalent variable substituents α-$R_{i-j}$ and β-$R_{i-k}$. When a bivalent variable, $R_i$, is defined to consist of two monovalent variable substituents, the convention used to define the bivalent variable is of the form "α-$R_{i-j}$:β-$R_{i-k}$" or some variant thereof. In such a case both α-$R_{i-j}$ and β-$R_{i-k}$ are attached to the carbon atom to give —C(α-$R_{i-j}$)(β-$R_{i-k}$)—. For example, when the bivalent variable $R_6$, —C(═$R_6$)— is defined to consist of two monovalent variable substituents, the two monovalent variable substituents are α-$R_{6-1}$:β-$R_{6-2}$, . . . α-$R_{6-9}$:β-$R_{6-10}$, etc, giving —C(α-$R_{6-1}$)(β-$R_{6-2}$)—, . . . —C(α-$R_{6-9}$)(β-$R_{6-10}$)—, etc. Likewise, for the bivalent variable $R_{11}$, —C(═$R_{11}$)—, two monovalent variable substituents are α-$R_{11-1}$:β-$R_{11-2}$. For a ring substituent for which separate α and β orientations do not exist (e.g. due to the presence of a carbon double bond in the ring), and for a substituent bonded to a carbon atom which is not part of a ring the above convention is still used, but the α and β designations are omitted.

Just as a bivalent variable may be defined as two separate monovalent variable substituents, two separate monovalent variable substituents may be defined to be taken together to form a bivalent variable. For example, in the formula —$C_1$($R_i$)H—$C_2$($R_j$)H— ($C_1$ and $C_2$ define arbitrarily a first and second carbon atom, respectively) $R_i$ and $R_j$ may be defined to be taken together to form (1) a second bond between $C_1$ and $C_2$ or (2) a bivalent group such as oxa (—O—) and the formula thereby describes an epoxide. When $R_i$ and $R_j$ are taken together to form a more complex entity, such as the group —X—Y—, then the orientation of the entity is such that $C_1$ in the above formula is bonded to X and $C_2$ is bonded to Y. Thus, by convention the designation " . . . $R_i$ and $R_j$ are taken together to form —$CH_2$—$CH_2$—O—CO— . . . " means a lactone in which the carbonyl is bonded to $C_2$. However, when designated " . . . $R_j$ and $R_i$ are taken together to form —CO—O—$CH_2$—$CH_2$— the convention means a lactone in which the carbonyl is bonded to $C_1$.

The carbon atom content of variable substituents is indicated in one of two ways. The first method uses a prefix to the entire name of the variable such as "$C_1$–$C_4$", where both "1" and "4" are integers representing the minimum and maximum number of carbon atoms in the variable. The prefix is separated from the variable by a space. For example, "$C_1$–$C_4$ alkyl" represents alkyl of 1 through 4 carbon atoms, (including isomeric forms thereof unless an express indication to the contrary is given). Whenever this single prefix is given, the prefix indicates the entire carbon atom content of the variable being defined. Thus $C_2$–$C_4$ alkoxycarbonyl describes a group $CH_3$—$(CH_2)_n$-O—CO— where n is zero, one or two. By the second method the carbon atom content of only each portion of the definition is indicated separately by enclosing the "$C_i$–$C_j$" designation in parentheses and placing it immediately (no intervening space) before the portion of the definition being defined. By this optional convention ($C_1$–$C_3$)alkoxycarbonyl has the same meaning as $C_2$–$C_4$ alkoxycarbonyl because the "$C_1$–$C_3$" refers only to the carbon atom content of the alkoxy group. Similarly while both $C_2$–$C_6$ alkoxyalkyl and ($C_1$–$C_3$)alkoxy($C_1$–$C_3$)alkyl define alkoxyalkyl groups containing from 2 to 6 carbon atoms, the two definitions differ since the former definition allows either the alkoxy or alkyl portion alone to contain 4 or 5 carbon atoms while the latter definition limits either of these groups to 3 carbon atoms.

II. DEFINITIONS

All temperatures are in degrees Centigrade.

TLC refers to thin-layer chromatography.

DCC refers to dicylcohexylcarbodiimide.

SDMS refers to siamyldimethylsilyl or (3-methylbut-2-yl)dimethylsilyl.

THF refers to tetrahydrofuran.

DMF refers to dimethylformamide.

Hunig's base refers to diisopropylethylamine, $[(CH_3)_2CH]_2N$—$CH_2CH_3$.

Saline refers to an aqueous saturated sodium chloride solution.

Chromatography (column and flash chromatography) refers to purification/separation of compounds expressed as (support; eluent). It is understood that the appropriate fractions are pooled and concentrated to give the desired compound(s).

IR refers to infrared spectroscopy.

CMR refers to C-13 magnetic resonance spectroscopy, chemical shifts are reported in ppm (δ) downfield from TMS.

NMR refers to nuclear (proton) magnetic resonance spectroscopy, chemical shifts are reported in ppm (δ) downfield from tetramethylsilane.

TMS refers to trimethylsilyl.

-φ refers to phenyl ($C_6H_5$).

$[\alpha]_D^{25}$ refers to the angle of rotation of plane polarized light (specific optical rotation) at 25° with the sodium D line (589A).

MS refers to mass spectrometry expressed as m/e, m/z or mass/charge unit. $[M+H]^+$ refers to the positive ion of a parent plus a hydrogen atom. EI refers to electron impact. CI refers to chemical ionization. FAB refers to fast atom bombardment.

HRMS refers to high resolution mass spectrometry.

Ether refers to diethyl ether.

Pharmaceutically acceptable refers to those properties and/or substances which are acceptable to the patient from a pharmacological/toxicological point of view and to the manufacturing pharmaceutical chemist from a physical/chemical point of view regarding composition, formulation, stability, patient acceptance and bioavailability.

When solvent pairs are used, the ratios of solvents used are volume/volume (v/v).

When the solubility of a solid in a solvent is used the ratio of the solid to the solvent is weight/volume (wt/v).

~ indicates that there are 2 possible orientations for the attached group, (1) α or β when attached to the steroid ring and (2) cis or trans when attached to a carbon atom of a double bond.

7-SDMS Baccatin III refers to 7-(3-methylbut-2-yl) dimethylsilyl baccatin III. 13-(N-(t-butylaminocarbonyl)-β-phenyl isoserinyl)-7-deoxy-$\Delta^{6,7}$-$\Delta^{12,13}$-iso-baccatin III is also known as 13-(N-(t-butylaminocarbonyl)-β-phenylisoserinyl)-7-deoxy-$\Delta^{6,12}$-iso-baccatin III.

EXAMPLES

Without further elaboration, it is believed that one skilled in the art can, using the preceding description, practice the present invention to its fullest extent. The following detailed examples describe how to prepare the various compounds and/or perform the various processes of the invention and are to be construed as merely illustrative, and not limitations of the preceding disclosure in any way whatsoever. Those skilled in the art will promptly recognize appropriate variations from the procedures both as to reactants and as to reaction conditions and techniques.

PREPARATION 1

N-(t-Butylaminocarbonyl)-β-phenyl isoserine methyl ester (2R,3S)-β-phenyl-isoserine methyl ester (4.35 g, 22 mM) is dissolved in dry THF (100 mL) and the flask cooled to 0°. To the mixture is added t-butyl isocyanate (2.8 mL, 25 mM). TLC after 15 minutes shows some starting material left so additional isocyanate (0.5 mL) is added. TLC after 1 hour shows no starting material so the solvent is concentrated under reduced pressure to give the title compound, NMR ($CDCl_3$, TMS) 1.27, 3.43, 3.81, 4.34, 4.48, 5.27, 5.32, 7.29 and 7.34 δ; MS (FAB-High Res.) theory for $C_{15}H_{22}N_2O_4$+H=295.1658, found=295.1663.

PREPARATION 2

(4S,5R)-N-(t-Butylaminocarbonyl)-2-(2,4-dimethoxyphenyl)-4-phenyl-5-oxazolidinecarboxylic acid methyl ester N-(t-butylaminocarbonyl)-β-phenyl isoserine methyl ester (PREPARATION 1, 68 mg, 0.23 mM) is dissolved in dry TBF (5 mL) and the solution treated with 2,4-dimethoxy benzaldehyde dimethyl acetal (70 mg, 0.33 mM) and pyridinium p-toluenesulfonate (6 mg, 0.02 mM) and the mixture warmed to reflux. Approximately 2 mL solvent is boiled away 3 times in a 45 minute period replenishing with 2 mL of fresh THF at which time TLC shows no starting material. The solvent is concentrated under reduced pressure and chromatographed (7 g of silica gel packed in ethyl acetate/1hexane, 1/3; elution with 80 mL ethyl acetate/hexane, 1/3; 45 mL ethyl acetate/hexane, 1/2; 30 mL ethyl acetate/hexane, 2/3 and 30 mL ethyl acetate/hexane, 1/1) to give the title compound: less polar isomer found in fractions 21–31—NMR ($CDCl_3$, TMS) 1.19, 3.82, 3.85, 3.89, 4.68, 4.88, 5.52, 6.46, 6.70 and 7.25–7.50 δ, MS (FAB-High Res.) theory for $C_{24}H_{31}N_2O_6$+H=443.2182, found=443.2172; more polar isomer in fractions 33–42—NMR ($CDCl_3$, TMS) 0.99, 3.53, 3.81, 3.88, 4.05, 4.55, 5.45, 6.48, 6.79 and 7.25–7.50 δ; MS (FAB-High Res.) theory for $C_{24}H_{31}N_2O_6$+H=443.2182, found=443.2180.

PREPARATION 3

(4S,5R)-N-(t-Butylaminocarbonyl)-2-(2,4-dimethoxyphenyl)-4-phenyl-5-oxazolidinecarboxylic acid potassium salt (4S,5R)-N-(t-Butylaminocarbonyl)-2-(2,4-dimethoxyphenyl)-4-phenyl-5-oxazolidinecarboxylic acid methyl ester (PREPARATION 2—less polar isomer, 6.27 g, 14.2 mM) is stirred at 20–25° under nitrogen in methanol (50 mL). To this mixture is added a solution of potassium carbonate (2.50 g, 18.1 mM) in water (6 mL). After 6 hr the reaction is concentrated under reduced pressure to remove the methanol and the residue freeze dried to give the title compound (admixed with potassium carbonate salts as a powder), NMR (DMSO-$d_6$, TMS) 1.10, 3.77, 4.17, 4.70, 5.16, 6.50, 6.60 and 7.14–7.42 δ.

PREPARATION 4

(4S,5R)-N-(t-Butylaminocarbonyl)-2-(2,4-dimethoxyphenyl)-4-phenyl-5-oxazolidinecarboxylic acid (4S,5R)-N-(t-Butylaminocarbonyl)-2-(2,4-dimethoxyphenyl)-4-phenyl-5-oxazolidinecarboxylic acid potassium salt (PREPARATION 3) is partitioned between methylene chloride and water containing hydrochloric acid (1 N, 0.9 mL). The phases are separated and the aqueous phase is reextracted with methylene chloride. The organic phases are combined, dried over sodium sulfate and concentrated to give the title compound.

PREPARATION 5

7-Triethylsilyl-$\Delta^{12,13}$-iso-baccatin III-13-(4S,5R)-N-(t-butylaminocarbonyl)-2-(2,4-dimethoxyphenyl)-4-phenyl-5-oxazolidinecarboxylic acid ester (4S,5R)-N-(t-Butylaminocarbonyl)-2-(2,4-dimethoxyphenyl)-4-phenyl-5-oxazolidinecarboxylic acid (PREPARATION 4, 3 mM) is dissolved in 20 mL methylene chloride (11 mL)-toluene (5 mL). To this is added 7-(triethylsilyl)-$\Delta^{12,13}$-iso-baccatin III (1.0 g, 20 mL 1.4 mM), 4-dimethylaminopyridine (93 mg, 0.76 mM) and 1,3-dicyclohexylcarbodimide (0.63 g, 3.1 mM) and the reaction mixture stirred for 3 hr under a nitrogen atmosphere. The reaction is diluted with toluene and filtered. The filtrate is washed with hydrochloric acid (1 N), aqueous sodium bicarbonate (5%) and saline. The organic phase is separated and dried over anhydrous sodium sulfate and concentrated. The product is purified by column chromatography (silica gel 60; acetonelhexane mixtures) to give the title compound, NMR ($CDCl_3$, TMS) 0.54, 0.90, 1.16, 1.17, 1.80, 1.89, 2.15, 2.18, 2.30, 2.50, 2.78, 3.83, 3.85, 3.91, 4.28, 4.38, 4.43, 4.64, 4.88, 5.04, 5.55, 5.65, 5.99, 6.49, 6.74, 7.22, 7.34–7.68 and 8.07 δ; CMR ($CDCl_3$, TMS) 5.27, 6.55, 8.99, 13.83, 14.11, 1892, 2090, 22.30, 28.79, 29.67, 32.86, 36.94, 38.75, 39.63, 50.59, 55.13, 55.28, 56.42, 58.40, 62.81, 72.50, 73.15, 74.10, 76.88, 80.58, 84.28, 85.81, 98.11, 104.94, 117.48, 122.28, 126.75, 127.66, 128.41, 128.49, 128.76, 129.76, 133.43, 139.81, 142.87, 154.95, 158.14, 161.68, 166.32, 168.33, 168.55, 170.12 and 204.76 δ.

PREPARATION 6

$\Delta^{12,13}$-Iso-baccatin III-13-(4S,5R)-N-(t-butylaminocarbonyl)-2(2,4-dimethoxyphenyl)-4-phenyl-5-oxazolidinecarboxylic acid ester 7-TES-$\Delta^{12,13}$-iso-baccatin III-13-(4S,5R)-N-(t-butylaminocarbonyl)-2-(2,4-dimethoxyphenyl)-4-phenyl-5-oxazolidinecarboxylic acid ester (PREPARATION 5, 460 mg, 0.413 mM) is dissolved in acetonitrile (0.5 mL) and the solution treated with triethylamine hydrofluoride (0.5 mL). The reaction is stirred at 20–25° for 6 hr. The reaction is then diluted with ethyl acetate and washed with aqueous sodium bicarbonate (5%), aqueous sodium bisulfate (5%) and saline. The organic phase is separated and dried over sodium sulfate and evaporated under reduced pressure. The crude product is purified by chromatography (50 g of HPLC grade silica gel eluting with 30% and 40% acetone in hexane) to give the title compound, NMR ($CDCl_3$, TMS) 1.07, 1.17, 1.32, 1.62, 1.67, 1.91, 2.16, 2.24, 2.31, 2.49, 2.81, 3.54, 3.71, 3.83, 3.92, 4.35, 4.65, 4.89, 5.06, 5.49, 5.58, 5.67, 6.47, 6.53, 6.73, 7.20, 7.34–7.65 and 8.07 (m, 2 H) δ; CMR ($CDCl_3$, TMS) 9.14, 13.83, 14.39, 19.85, 21.09, 22.50, 29.12, 29.93, 31.8, 33.2, 35.35, 38.69, 39.60, 50.92, 55.45, 55.82, 57.99, 63.16, 71.60, 73.68, 77.37, 77.72, 80.96, 84.62, 86.27, 98.43, 105.27, 117.5, 121.81, 127.02, 128.02, 128.76, 128.83, 130.09, 133.79, 140.2, 143.21, 155.4, 158.4, 162.1, 166.6, 168.7, 170.56, 172.0 and 206.74 δ.

PREPARATION 7

7-trifluoromethanesulfonyl-$\Delta^{12,13}$-iso-baccatin III 13-(4S,5R)-N-(t-butylaminocarbonyl)-2-(2,4-dimethoxyphenyl)-4-phenyl-5-oxazolidinecarboxylic acid ester A solution of $\Delta^{12,13}$-iso-baccatin III 13-(4S,5R)-N-(t-butylaminocarbonyl)-2-(2,4-dimethoxyphenyl)-4-phenyl-5-oxazolidinecarboxylic acid ester (PREPARATION 6, 63 mg, 0.063 mM) in methylene chloride (0.4 mL) and pyridine (0.15 mL) is cooled in a −78° bath. Trifluoromethanesulfonic anhydride (33 μL, 0.20 mM) is added resulting in the reaction solidifying. The reaction is warmed until it melts and then is re-cooled. After 1 hr the reaction is warmed to 20–25° and stirred 10 min. The reaction is poured into saturated aqueous ammonium chloride and the mixture is extracted with methylene chloride. The organic extract is washed with aqueous sodium bisulfite (1 M, 50 mL), dried and concentrated under reduced pressure. The residue is chromatographed (silica gel, 3 g, acetone/hexane, 30/70, 1 ml fractions, fractions 17 and 18) gives the title compound, NMR ($CDCl_3$, TMS) 1.11, 1.17, 1.77, 2.20, 2.21, 2.34, 2.68, 2.80, 2.95, 3.83, 3.88, 3.93, 4.34, 4.43, 4.67, 4.86, 5.05, 5.53, 5.60, 5.88, 6.47, 6.53, 6.72, 7.20, 7.30–7.70, and 8.07 δ; CMR ($CDCl_3$, TMS) 10.17, 14.12, 14.42, 19.71, 20.71, 22.36, 22.65, 29.10, 29.93, 31.59, 33.24, 38.75, 39.67, 50.93, 55.16, 55.44, 55.69, 57.57, 63.04, 72.95, 74.73, 77.20, 79.68, 80.87, 83.38, 85.86, 86.06, 98.38, 105.33, 117.61 122.78, 127.00, 127.98, 128.81, 130.09, 133.98, 140.17, 142.78, 155.29, 158.46, 162.06, 166.41, 168.91, 168.99, 170.90 and 203.44 δ.

PREPARATION 8

13-N-(t-Butylaminocarbonyl)-β-phenylisoserinyl)-7-deoxy-7δ,8δ-methano-$\Delta^{12,13}$-iso-baccatin III and 13-(N-t-butylaminocarbonyl)-β-phenylisoserinyl)-7-trifluoromethanesulfonyl-$\Delta^{12,13}$-iso-baccatin III A solution of 7-trifluoromethanesulfonyl-$\Delta^{12,13}$-iso-baccatin III 13-(4S,5R)-N-(t-butylaminocarbonyl)-2-(2,4-dimethoxyphenyl)-4-phenyl-5-oxazolidinecarboxylic acid ester (PREPARATION 7, 0.20 g, 0.18 mM) in 2 mL of acetic acid/methanol (80/20) is stirred at 20–25° for 1.3 hr. The reaction is diluted with ethyl acetate and washed with aqueous sodium bicarbonate (5%). The organic phase is dried over anhydrous sodium sulfate and concentrated. The crude product is chromatographed (silica gel 60; acetone/hexane mixtures), resulting in partial conversion to 7,19-methano-13-(N-t-butylaminocarbonyl-β-phenylisoserinyl)-$\Delta^{12,13}$-iso-baccatin III. The products eluting from this column are re-chromatographed in ethyl acetate/methylene chloride mixtures to give 13-N-(t-butylaminocarbonyl)-β-phenylisoserinyl)-7-trifluoromethanesulfonyl-$\Delta^{12,13}$-iso-baccatin III, NMR ($CDCl_3$, TMS) 1.09, 1.11, 1.17, 1.24, 1.76, 2.1, 2.18, 2.47, 2.65, 2.90, 3.83, 4.31, 4.43, 4.73, 4.88, 5.32, 5.47, 5.58, 5.85, 7.30–7.63 and 8.09 δ; CMR ($CDCl_3$, TMS) 10.09, 14.36, 19.69, 20.68, 22.62, 23.00, 29.13, 29.22, 29.73, 31.54, 33.01, 33.53, 38.67, 39.57, 50.68, 55.13, 55.41, 57.50, 72.79, 74.24, 74.66, 79.59, 83.30, 85.89, 122.70, 126.72, 127.99, 128.61, 128.81, 128.86, 130.22, 133.88, 138.65, 142.85, 156.47, 166.41, 168.98, 170.68, 171.16 and 203.40 δ and 13-N-(t-butylaminocarbonyl)-β-phenylisoserinyl)-7-deoxy-7δ,8δ-methano-$\Delta^{12,13}$-iso-baccatin III, NMR ($CDC_{13}$, TMS) 1.04, 1.12, 1.31, 1.55, 1.73, 2.17, 2.41, 2.55, 2.73, 2.91, 3.86, 4.09, 4.29, 4.41, 4.70, 4.78, 5.08, 5.21, 5.50, 5.62, 7.27–7.65, and 8.18 δ; CMR ($CDCl_3$, TMS) 12.80, 14.22, 20.86, 21.08, 22.44, 25.79, 28.77, 29.20, 30.09, 32.44, 32.81, 36.69, 39.70, 50.38, 55.03, 55.22, 74.39, 75.70, 78.29, 78.41, 78.87, 80.47, 85.15, 122.40, 126.65, 127.83, 128.77, 129.02, 130.38, 133.64, 139.15, 141.77, 156.19, 167.28, 169.76, 170.36, 171.02 and 203.64 δ.

PREPARATION 9

13-(N-(t-Butylaminocarbonyl)-β-phenyl isoserinyl)-7-deoxy-$\Delta^{6,7}$-$\Delta^{12,13}$-iso-baccatin III A mixture of 13-(N-(t-butylaminocarbonyl)-β-phenylisoserinyl)-7-trifluoromethanesulfonyl-$\Delta^{12,13}$-iso-baccatin III (PREPARATION 8) and 1,8-diazabicyclo[5.4.0]undec-7-ene in THF is stirred at 20–25° for 1 hr, at 500 for 2.5 hr, and at reflux temperature for 3 hr, after which reaction is complete. Ethyl acetate is added and the mixture washed with saturated aqueous sodium bicarbonate and with saline. The organic phase is dried over sodium sulfate, filtered and concentrated under reduced pressure. The residue is flash chromatographed (silica gel using a solution in methylene chloride for application to the column. The column is eluted with acetonitrile/methylene chloride mixtures) to give the title compound.

PREPARATION 10

7-Deoxy-$\Delta^{6,7}$-$\Delta^{12,13}$,-iso-baccatin III 13-(4S,5R)-N-(t-butylaminocarbonyl)-2-(2,4-dimethoxyphenyl)-4-phenyl-5-oxazolidinecarboxylic acid ester Following the general procedure of PREPARATION 9 and making non-critical variations but using 7-trifluoromethanesulfonyl-$\Delta^{12,13}$-iso-baccatin III 13-(4S, 5R)-N-(t-butylaminocarbonyl)-2-(2,4-dimethoxyphenyl)-4-phenyl-5-oxazolidinecarboxylic acid ester (PREPARATION 7), the title compound is obtained.

PREPARATION 11

13-[N-(t-Butylaminocarbonyl)-β-phenyl isoserinyl]-7-deoxy-$\Delta^{6,7}$-$\Delta^{12,13}$-iso-baccatin III 7-Deoxy-$\Delta^{6,7}$-$\Delta^{12,13}$-iso-baccatin III 13-(4S,5R)-N-(t-butylaminocarbonyl)-2-(2,4-dimethoxyphenyl)-4-phenyl-5-oxazolidinecarboxylic acid ester (PREPARATION 10) is stirred in a mixture of acetic acid/water (4/1) at 20–25° under an inert atmosphere for 4 days. The reaction is diluted with ethyl acetate and washed multiple times with water and aqueous sodium bicarbonate. The organic phase is dried over anhydrous sodium sulfate and concentrated. The product is chromatographed (silica gel 60, 230–400 mesh; acetone/hexane mixtures) to give the title compound.

Example 1

Ethyl 2-chloro-3-hydroxy-3-phenylpropionate (CII)

A solution of ethyl 2-chloro-3-oxo-3-phenylpropionate (CI, 100 g, 0.44 mol) and glacial acetic acid (25 ml, 0.44 mol) in ethanol 1 l) is cooled to −5° and stirred for 10 min. Sodium borohydride pellets (12.54 g, 0.33 mol, diam. 11 mm) are added in portions (4.2 g×3) with vigorous stirring. The reaction temperature is maintained at −5 to 0°. After the addition, the reaction mixture is stirred continuously at 0° for 5 hr and is then poured slowly into ice-water with stirring. The mixture is extracted with ethyl acetate (1 l). The organic phase is washed three times with water (100 ml) and saline (100 ml), dried over magnesium sulfate, and the solvent is removed under reduced pressure to give the title compound as a 1:4 mixture of the anti and syn isomers as determined by NMR, MS (m/z, CI+$NH_3$) 246 ($M^+$+17), 228 ($M^+$), 210, 194; "Anti" NMR (500 MHz, $CDCl_3$) 7.60–7.50, 5.33, 4.64, 4.33, 1.33 δ;. CMR (300 MHz, $CDCl_3$) 167.9, 138.2, 128.7, 128.5, 126.7, 74.6, 62.9, 62.2 and 13.7 δ; "Syn" NMR (500 MHz, $CDCl_3$) 7.60–7.50, 5.24, 4.58, 4.44 and 1.46 δ; CMR (300 MHz, $CDCl_3$) 168.9, 138.8, 126.7, 126.5, 126.9, 75.2, 62.3, 59.2 and 13.8 δ.

Example 2

Ethyl 2-chloro-3-hydroxy-3-phenylpropionate (CII)

A mixture of ethyl 2-chloro-3-oxo-3-phenylpropionate (CI, EXAMPLE 1, 6.8 g, 30 mmol) in dichloromethane (68 ml) is cooled to −50 and a solution of zinc borohydride (0.4 M, 38 ml, 15 mmol) in ether is added dropwise over 30 mins. After the addition, the reaction mixture is stirred at 0° for 30 mins and then poured into a cold solution (0°) of acetic acid (5 ml) in water (15 ml). The resulting mixture is extracted with dichloromethane (30 ml×2). The combined organic extracts are washed with water (30 ml), dried over magnesium sulfate, filtered and concentrated under reduced pressure. The residue is chromatographed (silica gel; ethyl acetate/hexane, (5/95 to 25/75) to give the title compound which is a 1:9 mixture of anti and syn isomers as determined by NMR.

Example 3

(2S,3R)-2-Chloro-3-hydroxy-3-phenylpropionic acid (CIV)

(±) Ethyl-2-chloro-3-hydroxy-3-phenyl propionate (CII, EXAMPLE 2, 5.5 g, 24 mmol, syn/anti=14:3) is incubated with lipase MAP-10 (1 g) in 0.2 M pH 7.0 phosphate buffer (100 ml). The reaction mixture is stirred vigorously at 25° for 6 days. The conversion is checked by HPLC (nucleosil c-18 column, acetonitrile/water 30/70, flow 2 ml/min and UV 207 nm) and showed starting material (60–65%, retention time 10.9 mins) and (2S,3R)-2-chloro-3-hydroxy-3-phenylpropionic acid (40–35%, retention time 1.0 mins). The resulting reaction mixture is acidified with hydrochloric acid (5%, 15 ml) to pH<2 and extracted with ethyl acetate (50 ml×3). The combined organic phase is extracted with aqueous potassium carbonate (10%7, 25 ml) and then washed with water (25 ml×2). The organic phase is dried over magnesium sulphate and concentrated under reduced pressure to give a mixture of halohydrins. The combined aqueous phase is washed with ether (30 ml) and acidified with hydrochloric acid (10%, 50 ml) to pH<2. The acidic mixture is extracted with ethyl acetate (50 ml×2). The organic phase is dried over magnesium sulphate and concentrated under reduced pressure to give the desired product. An analytical sample is prepared by recrystallizing the crude acid. The crude acid (6.7 g) is dissolved in hot chloroform (35 ml). To this solution heptane (10 ml) is added and the resulting mixture is cooled to 0° for 1 hr which produces a solid which is the title compound, mp=98–100°; $[\alpha]^{25}_D$=+1.95° (c=1.48, methanol) and −3.9° (c=1.5, $CHCl_3$); NMR (300 MHz, $CDCl_3$) 7.42–7.39, 5.28 and 4.58 δ; MS (m/z) 200 (M+), 165, 147, 129, 119, 107, 91, 79, 65 and 51; HRMS calculated for $C_9H_9O_3Cl$=200.0240, observed=200.0240.

Example 4

Methyl (2S,3R)-2-chloro-3-hydroxy-3-phenylpropionate (CV)

A mixture of (2S,3R)-2-chloro-3-hydroxy-3-phenyl propionic acid (CIV, EXAMPLE 3, 2 g, 10 mmol) in methanol (20 ml, saturated with hydrochloric acid) is stirred at 25° for 1 hr. The reaction mixture is poured into a saturated aqueous sodium bicarbonate (20 ml) and extracted with ethyl acetate (20 ml×3). The combined organic phases are washed with water (20 ml) and dried over magnesium sulfate. Filtration and solvent removal under reduced pressure gives the title compound, $[\alpha]^{25}_D$=−5.0° (c=1.5, $CHCl_3$); NMR (300 MHz, $CDCl_3$) 7.41–7.35, 5.19, 4.51 and 3.70 δ; CMR (300 MHz, $CDCl_3$) 168.4, 138.1, 128.7, 128.5, 126.5, 74.4, 62.8 and 53.0 δ.

Example 5

Methyl (2R,3R)-2,3-epoxy-3-phenylpropionate (CVI)

To a mixture of (2S,3R)-methyl-2-chloro-3-hydroxy phenylpropionate (CV, EXAMPLE 4, 31.6 g, 0.15 mol) in DMF (730 ml) is added water (13.5 ml) followed by potassium carbonate (62 g, 0.45 mol) at 25° with stirring. The mixture is allowed to stir at 25° for 72 hr and then poured into a mixture of ethyl acetate (3 l) and water (500 ml). The organic phase is separated and the aqueous phase is back washed with ethyl acetate (400 ml×2). The combined organic phases are washed with water (400 ml×3). The aqueous phases are extracted with ethyl acetate (100 ml). The combined organic phase is dried over anhydrous magnesium sulfate, filtered and concentrated under reduced pressure to about 800 ml, the organic mixture is again washed with water (250 ml×4). The organic phase is dried over magnesium sulfate, filtered and the solvent removed under reduced pressure to give the title compound, $[\alpha]^{25}_D$=+

15.0° (c=1.52, chloroform); NMR (300 MHz, $CDCl_3$) 7.45–7.33, 4.30, 3.88 and 3.58 δ; CMR (300 MHz, $CDCl_3$) 167.0, 132.7, 128.5, 128.0, 126.5, 57.5, 55.8 and 52.0 δ; MS (m/z) 178 (M+), 161, 131, 107, 105, 91, 79, 77 and 51.

Example 6

Methyl (2R,3S)-3-amino-2-hydroxy-3-phenylpropionamide (CVII)

Methyl (2R,3R)-2,3-epoxy-3-phenylpropionate (CVI, EXAMPLE 5, 21.2 g, 0.12 mol) is added to a cold (0°) solution of ammonium hydroxide (220 ml, 30%) with stirring (addition took about 30 mins). The reaction mixture is then stirred at 25° for 4 days. The resulting mixture is concentrated to dryness under house vacuum in a 30–35° water bath to give a the crude product. An analytical sample is prepared by recrystallization. The crude product (2 g) is dissolved in refluxing methanol (30 ml). After 15 mins of refluxing, the suspension is filtered at the boiling temperature and a solid collected which did not dissolve in methanol. The filtrate is kept in the freezer at −20° overnight to give the first crop of crystals (730 mg). The mother liquor is evaporated under house vacuum to reduce the volume to about 10 ml. After standing at −20°, a second crop of crystals (500 mg) is obtained, mp=175–178°; $[\alpha]^{25}_D$=+60° (c=0.66, methanol); IR (mineral oil) 3425, 3416, 3139, 1640, 1451, 1316, 996, 971 and 647 $cm^{-1}$; NMR (300 MHz, DMSO-$d_6$/$D_2O$ 3/1) 7.13–7.36, 4.10 and 3.88 δ; CMR (300 MHz, DMSO-$d_6$/$D_2O$ 3/1) 174.8, 144.1, 127.7, 127.0, 126.3, 75.5 and 57.2 δ; MS (m/z) 181 ($M^+$+1), 164, 106 and 105; HRMS (m/z) calculated for $C_9H_{12}N_2O_2+H_1$=181.0977, observed=181.0975.

Example 7

Isobutyl (2R,3S)-3-amino-2-hydroxy-3-phenylpropionate (I)

To a mixture of crude (2R,3S)-2-hydroxy-3-amine-3-phenylpropionamide (CVII, EXAMPLE 6, 180 mg, 1 mmol) in isobutyl alcohol (2.5 ml) is bubbled anhydrous hydrogen chloride gas until saturated allowing the temperature to rise. The reaction mixture is then heated to 100° overnight. The resulting solution is evaporated to dryness under house vacuum at 50°. The residue is dissolved in water (5 ml), and the aqueous is neutralized with saturated potassium carbonate solution to pH>9. The basic aqueous is extracted with ethyl acetate (15 ml×3). The combined organic phase is dried over magnesium sulfate, filtered and the solvent removed under reduced pressure. The residue is purified by flash chromatography (methanol/dichloromethane, 1/5) to give the title compound, NMR (300 MHz, $CDCl_3$) 7.44–7.28, 4.34, 4.30, 4.00, 1.95 and 0.95 δ; CMR (300 MHz, $CDCl_3$) 173.5, 142.3, 128.5, 127.5, 126.7, 75.0, 71.8, 58.0, 27.6 and 18.9 δ; MS (m/z) 238 ($M^+$+1), 165, 136, 118, 107, 106, 104, 91, 79, 77 and 57; HRMS (m/z) calculated for $C_{13}H_{19}N_1O_3+H_1$=238.1443, observed=238.1441.

Example 8A (S)-N-(4-Nitrobenzenesulfonyl)phenylglycine methyl ester (CCII)

(S)-phenylglycine methyl ester hydrochloride (CCI, 2.01 g, 10 mnmol) is added to pyridine (20 mL) and diisopropylethylamine (7.0 mL, 40 mmol). The mixture is cooled to −10° and treated dropwise over 45 min with a solution of 4-nitrobenzesulfonyl chloride (3.33 g, 15 mmol) dissolved in methylene chloride (20 mL). After 1 hr the reaction is treated with water (0.5 mL) and stirred an additional 30 min. The reaction is then poured into methylene chloride, ice and aqueous hydrochloric acid (3N). The methylene chloride layer is separated and extracted with aqueous sodium bicarbonate (5%). The methylene chloride layer is then dried over magnesium sulfate and concentrated under reduced pressure (less than 30 mm Hg). The concentrate is crystallized from methanol, collecting two crops to give the title compound, TLC (silica gel GF) $R_f$=0.43 (ethyl acetatettoluene, 1/9).

Example 8D (S)-N-(2,4-Dinitrobenzenesulfonyl)-phenylglycine methyl ester (CCII)

Following the general procedure of EXAMPLE 8A and making noncritical variations but using 2,4-dinitrobenzenesulfonyl chloride (3.20 g, 12 mmol) the title compound is obtained, TLC (silica gel GF) $R_f$=0.60 in (ethyl acetate/toluene, 1/9).

Example 8E (S)-N-(Benzoyl)phenylglycine methyl ester (CCII)

Following the general procedure of EXAMPLE 8A and making noncritical variations but using benzenesulfonyl chloride, the title compound is obtained.

Example 9E

2-Hydroxy-(3S)-(benzamido)-3-phenylpropionitrile (CCIII)

(S)-N-(Benzoyl)phenylglycine ethyl ester (CCII, EXAMPLE 8E, 16.52 g, 58.31 mmol) is added to tetrahydrofuran (76 mL) and the mixture cooled to −78° under a nitrogen atmophere. To this is added diisobutyl aluminum hydride (neat, 26 mL, 145.9 mmol) over 40 min. After an additional 30 min, the reaction is warmed to −65° and treated with a solution of potassium cyanide (37.77 g, 580 mmol) dissolved in water (65 mL), followed by methanol (30 mL) and acetic acid (95 mL). The reaction is then allowed to warm to 20–25° and stirred for 1 additional hr. The reaction is then partitioned between ethyl acetate and water. The organic phase is separated, washed with aqueous hydrochloric acid (10%), water, saline and dried over sodium sulfate. Concentration of the organic mixture gives, after co-evaporation with toluene the title compound, TLC (silica gel GF) $R_f$=0.31 in (ethyl acetate/cyclohexane, 1/1).

Example 10E($C_2$)

(3S)-N-benzoyl-3-phenylisoserine ethyl ester (II)

(3S)-(benzamido)-3-phenylpropionitrile (CCIII, EXAMPLE 9E, 0.29 g, 1.09 mmol) is dissolved in ethanol (2 mL) and the solution treated with hydrochloric acid (6.25 N, 1 mL). After 20 hr at 20–25° the reaction is treated with water (5 mL) and stirred an additional 2 hr. The reaction is then partitioned between ethyl acetate and water. The ethyl acetate layer is separated, dried over sodium sulfate and concentrated under reduce pressure to give the title compound, TLC (silica gel GF) $R_f$=0.31 (ethyl acetate/cyclohexane, 1/1; starting material in the same system $R_f$=0.31); NMR ($CDCl_3$, TMS) 8.140, 7.877, 7.412, 5.484, 4.862 δ.

Example 10E($C_1$)

(3S)-N-benzoyl-3-phenylisoserine methyl ester (II)

Following the general procedure of EXAMPLE 10E($C_2$) and making non-critical variations but using methanol the title compound is obtained, TLC (silica gel GF) $R_f$=0.31 (ethyl acetate/cyclohexane, 1/1, starting material in the in the same system $R_f$=0.31); anti isomer NMR ($CDCl_3$) 8.010, 7.791, 7.309, 5.534, 4.615, 3.581 δ; syn isomer NMR ($CDCl_3$) 7.752, 7.698, 7.303, 5.639, 4.508, 3.685 δ.

Example 10C (3S)-N-(9-anthracenesulfonyl)-3-phenylisoserine methyl ester (II)

Following the general procedure of EXAMPLE 10E($C_2$) and making non-critical variations but using (9-anthracenesulfonamido)-3-phenylpropionitrile (CCIII), the title compound is obtained.

Example 11A

Methyl (2R,3S)-3-(4-nitrobenzenesulfonamido)-3-phenyl-2-hydroxypropionate (II)

Triethylamine (4.8 ml, 34.4 mmol) is added to a stirred solution of methyl (2R,3S)-phenylisoserinate (I, PREPARATION 7, 7.26 g, 31.3 mmol) in methylene chloride (80 ml) at 0°. To this slurry of is added trimethylsilyl chloride (4.4 ml, 34.7 mmol). Additional methylene chloride (45 ml) is added. The mixture is cooled to −65° and triethylamine (9.8 ml, 70.3 mmol) is added. p-Nitrophenysulfonyl chloride (6.93 g, 31.3 mmol) is added. The reaction rate is too slow at −65° so the temperature is gradually raised to 0°. Hydrogen fluoride (10% aqueous, 5 equivalents) is added. The aqueous phase is separated from the organic (methylene chloride) phase and methanol is added to the organic phase. The methylene chloride is removed under reduced pressure and the title compound is obtained, mp=187–189°; NMR ($CDCl_3$) 8.05, 7.43, 7.11, 4.92, 4.34, 3.79 and 3.44 δ; CMR ($CDCl_3$) 172.4, 149.6, 137.0, 128.4, 128.2, 128.1, 127.3, 123.8, 74.5, 60.2 and 52.9 δ; HRMS found 381.0749 (calcd for $C_{16}H_{16}N_2O_7S$ ($MH^+$) 381.0756); $[\ ]_D^{25}$=−4.8°.

Example 11B

Methyl (2R,3S)-2-benzthiazolesulfonamido-3-phenyl-2-hydroxypropionate (II)

Sodium bicarbonate (2.8 g, 33 mmol) and 2-sulfonylchloride-benzthiazole (5 g wet, ca. 11 mmol) is added to a suspension of methyl (2R,3S)-phenylisoserinate (I, PREPARATION 7, 2.53 g, 11 mmol) in THF/water (1/1, 40 ml). The reaction mixture is stirred at 20–25° for 30 mins. Water (20 ml) is added and the mixture is extracted with ethyl acetate (2×50 ml). The combined organic phases are washed with water (30 ml) again, dried over magnesium sulfate and concentrated under reduced pressure. The concentrate is chromatographed (silica gel column; methanol/methylene chloride (5/95) to give the title compound, mp=170–171°; $[\alpha]^{25}_D$=−1.9° (c=0.69, methanol); IR (mineral oil) 3244, 1735, 1476, 1450, 1422, 1349, 1240, 1160 and 1069 $cm^{-1}$; NMR (300 MHz, DMSO-$d_6$) 9.33, 8.12, 7.99, 7.55, 7.20, 7.01, 5.73, 4.82, 4.25 and 3.41 δ; CMR (300 MHz, DMSO-$d_6$) 171.5, 166.8, 151.6, 137.7, 135.8, 127.5, 127.2, 124.2, 122.8, 74.1, 60.8 and 51.5 δ; MS (m/z) 393 ($M^+$+1), 333, 303, 215, 196, 134, 106; HRMS (m/z) calculated for $C_{17}H_{16}N_2O_5S_2+H_1$=393.0579, observed=393.0572.

Example 11C-1

Methyl (2R,3S)-3-(9-anthracenesulfonamido)-3-phenyl-2-hydroxypropionate (II)

To a suspension of methyl (2R,3S)-phenylisoserinate (I, PREPARATION 7, 40 mg, 0.2 mmol) in THF/water (1/1, 2 ml) is added sodium bicarbonate (34 mg, 0.4 mmol) and anthracene-9-sulfonyl chloride (88 mg, 0.3 mmol). This reaction mixture is stirred at 25° for 12 hr. Water (2 ml) is added and the mixture is extracted with ethyl acetate (10 ml×2). The combined organic phase is washed with saturated potassium carbonate (3 ml) and water (5 ml), dried (magnesium sulfate), and concentrated under reduced pressure. The residue is chromatographed (silica gel; ethyl acetate/hexane (1/1)) to give the title compound, mp=98–102°; $[\alpha]^{25}_D$=+7.2° (c=0.76, $CHCl_3$); IR (mineral oil) 3469, 3297, 1742, 1330, 1285, 1260, 1245, 1230, 1160, 1150, 1115, 1090, 1063, 781, 742 and 703 $cm^{-1}$; NM (300 MHz, $CDCl_3$) 9.23, 8.48, 7.95, 7.68–7.63, 7.53–7.48, 6.84, 6.68, 6.62, 6.08, 4.82, 4.19, 3.59 and 3.19 δ; CMR (300 MHz, DMSO-$d_6$) 172.3, 136.1, 135.3, 131.0, 130.0, 129.3, 129.6, 128.7, 127.5, 127.4, 126.2, 125.1, 124.7, 73.9, 59.1 and 53.0 δ; MS (m/z) 436 ($M^+$+1), 435 ($M^+$), 388, 354, 346, 258, 241, 209, 196, 193, 177, 119 and 106; HRMS (m/z) calculated for $C_{24}H_{21}N_1O_5S_1$=435.1140, observed=435.1150.

Example 11C-2

Methyl (2R,3S)-3-(9-anthracenesulfonamido)-3-phenyl-2-hydroxypropionate (II)

(3S)-3-Phenylisoserine methyl ester (I, 0.38 g, 1.95 mmol) is dissolved in methylene chloride (5 mL) and pyridine (1 mL) and the solution treated with a suspension of 9-anthracenesulfonylchloride (0.536 g, 1.95 mmol). The reaction is stirred at 23° for 90 min. The reaction is then poured into methylene chloride and extracted with hydrochloric acid (1 N) and aqueous bicarbonate (5%) and dried over magnesium sulfate. Concentration of the organic layer under reduced pressure produces crude product. This concentrate is chromatographed (silica gel 60; ethyl acetate/toluene, 20/80) to give the title compound, TLC (silica gel GF) $R_f$=0.38 in (ethyl acetate/toluene, 2/8); NMR($CDCl_3$, TMS) 3.11, 3.57, 4.18, 4.78, 6.22, 6.59, 6.67, 7.50, 7.55–7.75, 7.92, 8.09, 8.47 and 9.15 δ

Example 12A (2S,4S,5R)-2,4-Diphenyl-3-(4-nitrobenzenesulfonamido)-5-methoxycarbonyl-1,3-oxazolidine (III)

Benzaldehyde dimethylacetal (200 μl, 1.33 mmol) and a catalytic amount of p-toluenesulfonic acid (37 mg) are added to methyl (2R,3S)-3-(4-nitrobenzenesulfonamido)-3-phenyl-2-hydroxypropionate (II, EXAMPLE 11A, 315 mg, 0.83 mmol) in toluene 5 ml. The mixture is heated at 100° under reduced pressure (15 mm mercury) with no condenser. The reaction is complete after 1 hr. The crude reaction mixture is diluted with ethyl acetate and washed with water (2×). After drying the organinc layer over magnesium sulfate the crude material is purified by column chormatography (silica gel; eluting with ethyl acetate/cyclohexane, 35/65) to give the title compound, mp=118–120°.

Example 12B (2R,4S,5R)- and (2S,4S,5R)-2,4-Diphenyl-3-benzothiazolesulfonamido-5-methoxycarbonyl-1,3-oxazolidine (III-R/S, diasteriomeric mixture of R and S diasteriomers at $C_2$)

A mixture of methyl (2R,3S)-3-benzothiazolesulfonamido-3-phenyl-2-hydroxypropionate (II, EXAMPLE 11B, 3.45 g, 8.8 mmol) in dry toluene (100 ml) is treated with benzaldehyde dimethylacetal (4 ml, 26.4 mmol) in the presence of a catalytic amount of p-toluenesulfonic acid (170 mg, 0.9 mmol) and stirred at 105° under reduced pressure (15 inches mercury for 2 hr). TLC analysis (silica gel; ethyl acetate/hexane, 30/70) shows two products: a major product with $R_f$=0.43, and a minor product with $R_f$=0.37. The resulting reaction mixture is diluted with ethyl acetate (50 ml) and washed with water (50 ml). The aqueous phase is extracted again with ethyl acetate (50 ml). The combined organic phases are dried over magnesium sulfate, filtered and the solvent removed under reduced pressure. Purification by column chromatography (silica gel; ethyl acetate/hexane (10/90)) gives the title compounds, "(2R)-" mp=145–147°; $[\alpha]^{25}_D$=+81.50° (c=0.60, $CHCl_3$); IR (mineral oil) 1739, 1450, 1433, 1320, 1255, 1228, 1204, 1172, 1132 and 1107 $cm^{-1}$; NMR (500 MHz, DMSO-$d_6$) 8.20, 8.10, 7.70, 7.62, 7.43, 7.30, 7.18, 6.70, 5.72, 4.99 and 3.63 δ; CMR (500 MHz, DMSO-$d_6$) 168.8, 166.5, 151.4, 137.6, 135.9, 134.9, 130.0, 128.9, 128.3, 127.9, 127.7, 127.6, 124.5, 122.7, 92.8, 81.7, 65.8 and 52.4 δ; MS (m/z) 481 ($M^+$+1), 375, 340, 310, 303, 284, 261, 194, 167, 133, 121 and 91; HRMS (m/z) calculated for $C_{24}H_{20}N_2O_5S_2$+$H_1$=481.0892, observed=481.0903: "(2S)-" mp=127–130°; $[\alpha]J^{25}_D$=+43.22° (c=0.31, $CHCl_3$); IR (mineral oil) 1758, 1738, 131 1212, 1172, 1125, 1093, 1043 and 1029 $cm^{-1}$; NMR (500 MHz, DMSO-$d_6$) 8.39, 8.38, 7.76, 7.52, 7.46, 6.50, 5.54, 5.12 and 3.23 δ; CMR (300 MHz, $CDCl_3$) 168.9, 162.7, 152.8, 138.1, 136.6, 129.4, 128.7, 128.5, 128.3, 128.1, 127.9, 127.6, 127.3, 127.1, 125.5, 122.2, 93.5, 82.4, 65.6 and 52.4 δ; MS (m/z) 481 ($M^+$+1) 463, 417, 385, 375, 310, 303, 282, 265, 224, 194, 162 and 121; HRMS (m/z) calculated for $C_{24}H_{20}N_2O_5S_2$+$H_1$=481.0892, observed=481.0898.

Example 12C(S)

(2S,4S,5R)-2,4-diphenyl-3-(9-anthracenesulfonamido)-5-methoxycarbonyl-1,3-oxazolidine (III)

Following the general procedure of EXAMPLES 9A and making non-criticical variations but starting with methyl (2R,3S)-3-(9-anthracenesulfonamido)-3-phenyl-2-hydroxypropionate (II, EXAMPLE 11C, 220 mg, 0.5 mmol), the title compound is obtained, mp=169–171°; IR (mineral oil) 1755, 1749, 1312, 1304, 1243, 1229, 1218, 1146, 1113, 1105, 997, 987, 736, 696 and 680 $cm^{-1}$; NMR (300 MHz, $CDCl_3$) 9.12, 8.44, 7.87, 7.46, 7.19–7.05, 6.96, 6.57, 5.59, 4.85 and 3.89 δ; CMR (300 MHz, $CDCl_3$) 169.6, 138.4, 137.1, 135.7, 131.3, 130.7, 129.0, 128.9, 128.8, 128.7, 128.2, 127.9, 127.5, 127.4, 127.2, 125.4, 125.2, 125.0, 93.3, 82.3, 64.5 and 52.7 δ; MS (m/z) 524 ($M^+$+1), 523 ($M^+$), 346, 282, 254, 241, 209, 193, 178, 165, 105 and 91; HRMS (m/z) calculated $C_{31}H_{25}N_1O_5S_1$+$H_1$=524.1531, observed=524.1525.

Example 12C(R)

(2R,4S,5R)-2,4-diphenyl-3-(9-anthracenesulfonamido)-5-methoxycarbonyl-1,3-oxazolidine (III)

A suspension of methyl (2R,3S)-3-(9-anthracenesulfonamido)-3-phenyl-2-hydroxypropionate (II, EXAMPLE 11C, 45 mg, 0.1 mmol) in dry toluene (1 ml) is treated with benzaldehyde dimethylacetal (45 μl, 0.3 mmol) in the presence of a catalytic amount of pyndinium toluenesulfonate (2.5 mg, 0.01 mmol) and stirred at 75° under reduced pressure of 15 inch/mercury for 2 hr. HPLC analysis (silica gel with a C-18 group attached; acetonitrile/water, 65/35, flow 1 ml/min and UV 254 nm) showed the final product (70.2%, retention time 15.0 mins) and the (3S)-diasteriomer (3.5%, retention time 17.0 mins). The resulting reaction mixture is diluted with ethyl acetate (15 ml) and washed with water (10 ml). The aqueous phase is extracted again with ethyl acetate (10 ml). The combined organic phase is dried over magnesium sulfate, filtered and the solvent is removed under reduced pressure. Purification by silica gel column chromatography (ethyl acetate/hexane, 10/90) gives the title compound, mp=71–73°; IR (mineral oil) 1762, 1737, 1332, 1216, 1158, 1146, 1116, 1106, 1089, 1076, 1027, 755, 739, 697 and 681 $cm^{-1}$; NMR (300 MHz, $CDCl_3$) 9.02, 8.39, 7.86, 7.57–7.50, 7.43, 7.30–7.25, 7.07, 6.88, 6.67–6.51, 6.51–6.44, 6.27, 5.94, 4.84 and 3.77 δ; CMR (300 MHz, $CDCl_3$) 170.0, 137.1, 136.2, 133.5, 130,9, 130.5, 128.9, 128.8, 128.6, 128.1, 128.0, 126.9, 125.2, 124.9, 93.1, 81.6, 68.7 and 52.6 δ; MS (m/z) 524 ($M^+$+1), 523 (M+), 369, 354, 346, 282,265, 241, 209, 193, 178, 165, 121 and 91; HRMS (m/z) calculated $C_{31}H_{25}N_1O_5S_1$+$H_1$=524.1531, observed=524.1530.

Example 13A (2S,4S,5R)-2,4-diphenyl-3-(4-nitrobenzenesulfonamido)-5-carboxy-1,3-oxazolidine (IV)

Water (8 ml), methanol (8 ml) and TBF (8 ml) are added to (2S,4S,5R)-2,4-diphenyl-3-(4-nitrobenzenesulfonamido)-5-methoxycarbonyl-1,3-oxazolidine (III, EXAMPLE 12A, 1.50 g 3.19 mmol). Potassium carbonate (1.018 g, 7.71 mmol) is then added. The resulting mixture is stirred at 20–25° until complete by TLC. After 5 hr the reaction is complete and the reaction mixture is extracted with basic methylene chloride (2×). The aqueous phase is then acidified with hydrochloric acid and extracted with ethyl acetate. The ethyl acetate phase is then washed with water, saline and dried over magnesiuim sulfate. Concentration of the organic phase (ethyl acetate) gives the title compound, mp=61–65°.

Example 13B (2R,4S,5R)- and (2S,4S,5R)-2,4-diphenyl-3-benzothiazolesulfonamido-5-carboxy-1,3-oxazolidine (IV, diasteriomeric mixture of R and S diasteriomers at $C_2$)

A suspension of (2R,4S,5R) and (2S,4S,5R)-2,4-diphenyl-3-benzothiazolesulfonamido-5-methoxycarbonyl-1,3-oxazolidine (III, EXAMPLE 12B, 100 mg, 0.2 mmol) in THF/methanol/water (1/1/1, 3 ml) is treated with potassium carbonate (100 mg, 0.73 mmol) and stirred at 25° for 3 hr. The resulting basic reaction mixture is diluted with water (15 ml) and washed with ethyl acetate (15 ml). The aqueous phase is then acidified with hydrochloric acid (10%) to pH<2, and extracted with ethyl acetate (2×15 ml). The combined organic phases are dried over magnesium sulfate, filtered, and the solvent removed under reduced pressure to give the title compound, "(2R)-" mp=64–66°; $[\alpha]^{25}_D$=+47.4° (c=0.61, $CHCl_3$) (mineral oil) 3064, 3034, 1761, 1414, 1368, 1316, 1237, 1211, 1171, 1128, 1100, 1076, 1028 and 761 $cm^{-1}$; NMR (300 MHz, MeOD) 8.19, 7.92, 7.67, 7.60, 7.50, 7.26–7.10, 6.66, 5.83 and 4.81 δ; CMR (300 MHz, MeOD) 172.8, 169.1, 153.7, 140.2, 138.3, 137.1, 131.1, 130.7, 130.0, 129.8, 129.5, 129.2, 128.9, 126.3, 123.6, 95.5, 84.8 and 68.7 δ; MS (m/z) 467 ($M^+$+1) 450, 421, 333, 303, 297, 296, 270, 212, 194, 132, 121 and 107; HRMS (m/z)

calculated for $C_{23}H_{18}N_2O_5S_2+H_1$=467.0735, observed=467.0739 and "(2S)-" mp=60–61°; $[\alpha]^{25}_D$=+33.5° (c=0.37, $CHCl_3$); IR (mineral oil) 3064, 3034, 1763, 1401, 1377, 1213, 1196, 1173, 1086, 1077 and 700 $cm^{-1}$; NMR (300 MHz, MeOD) 8.27, 8.14, 7.72–7.09, 6.72, 5.62 and 4.72 δ; CMR (300 MHz, MeOD) 174.5, 164.9, 154.4, 141.0, 139.2, 138.3, 130.8, 129.9, 129.7, 129.5, 129.3, 129.1, 128.9, 126.8, 124.0, 94.8, 85.2 and 67.8 δ; MS (m/z) 467 ($M^+$+1) 450, 362, 324, 297, 296, 270, 208, 194, 148, 132, 121 and 107; HRMS (m/z) calculated $C_{23}H_{18}N_2O_5S_2+H_1$=467.0735, observed=467.0730.

Example 13C (2S,4S,5R)-2,4-diphenyl-3-(9-anthracenesulfonamido)-5-carboxy-1,3-oxazolidine (IV)

Following the general procedure of EXAMPLES 13A and 13B and making non-criticical variations but starting with (2R,4S,5R)-2,4-diphenyl-3-(9-anthracenesulfonamido)-5-methoxycarbonyl-1,3-oxazolidine [III-R, EXAMPLE 9C(R), 210 mg, 0.4 mmol), the title compound is obtained, NMR (300 MHz, $CDCl_3$) 9.19, 8.50, 7.89, 7.52–7.45, 7.16–7.08, 7.00, 6.65, 5.61 and 4.88 δ; CMR (300 MHz, $CDCl_3$) 138.4, 137.1, 135.7, 131.3, 130.7, 129.1, 128.9, 128.8,128.2, 127.9, 127.3, 127.1, 125.2, 125.0, 93.3, 82.3 and 64.5 δ; MS (m/z) 509 ($M^+$), 194, 178, 176, 151, 105, 89, 76 and 64.

Example 14A

7-SDMS baccatin III 13-(2R,4S,5R)- and (2S,4S,5R)-2,4-diphenyl-3-(4-nitrobenzenesulfonamido)-1,3-oxazolidine-5-carboxylic acid ester (VII)

(2S,4S,5R)-2,4-Diphenyl-3-(4-nitrobenzenesulfonamido)-5-carboxy-1,3-oxazolidine (IV, EXAMPLE 13A, 323 mg, 0.711 mmol) is mixed with toluene (2.5 ml) at 20–25°. DDC (160 mg, 0.775 mmol) is then added to the reaction mixture. 7SDMS Baccatin III (VI, 156 mg, 0.218 mmol) is added followed by DMAP (35 mg, 0.286 mmol) and the reaction mixture is stirred at 20–25° until complete (1 hr) by TLC. Sodium bicarbonate (50% aqueous, 10 ml) and more toluene (5 ml) is added to the reaction mixture and then stirred at 20–25° for 2 hrs. The reaction mixture is filtered through a medium frit to remove the urea byproduct. After filtering the phases are separated and the aqueous phase is extracted with ethyl acetate. The combined organic phases are washed with aqueous sodium bicarbonate (50%), water and saline. The organic phases are dried over magnesium sulfate, filtered and then concentrated. The concentrate is purified by column chromatograpy (silica gel; eluting with ethyl acetate/cyclohexane, 20/80) to give the title compound, $R_f$=0.3 (ethyl acetate/cyclohexane, 30/70).

Example 14B

7-SDMS baccatin III 13-(2R,4S,5R)- and (2S,4S,5R)-2,4-diphenyl-3-benzothiazolesulfonamido-1,3-oxazolidine-5-carboxylic acid ester (VII)

A suspension of (2R,4S,5R)- and (2S,4S,5R)-2,4-diphenyl-3-benzothiazolesulfonamido-5-carboxy-1,3-oxazolidine (IV, EXAMPLE 13B, (269 mg, 0.58 mmol) and 7-SDMSBac(III) (107 mg, 0.15 mmol) in toluene (2 ml) is added DMAP (8 mg, 0.06 mmol) and DCC (105 mg, 0.51 mmol) and stirred at 25° for 4 hr. To the reaction mixture water (10 ml) is added and the product extracted with ethyl acetate (10 ml×3). The combined organic phases are dried over magnesium sulfate, filtered, and the solvent is removed under reduced pressure. Purification by column chromatography (silica gel; ethyl acetate/hexane, (20/80)) gives the title compound as a diasteriomer mixture of (2R)- and (2S)-, NMR (500 MHz, $CDCl_3$) 8.16, 8.03, 7.77, 7.60, 7.60–7.45, 7.25, 7.15, 6.70, 6.33, 6.15, 5.90, 5.63, 4.80, 4.79, 4.31, 4.21, 4.09, 3.72, 3.46, 2.19 and 2.08 δ; CMR (500 MHz, $CDCl_3$) 201.6, 169.7, 169.1, 168.5, 167.1, 166.7, 152.0, 140.0, 137.5, 136.6, 134.6, 133.7, 130.1, 130.0, 129.2, 129.0, 128.8, 128.7, 128.6, 128.1, 128.0, 127.4, 127.2, 125.2, 121.6, 94.3, 84.2, 83.4, 80.8, 79.1, 76.3, 75.0, 74.9, 72.4, 72.2, 72.0, 66.5, 58.4, 49.2, 46.8, 43.2, 37.4, 35.4, 33.9, 29.7, 28.3, 26.4, 25.6, 24.9, 21.7, 20.9, 14.0 and 10.2 δ; Ms (m/z) 1163 ($M^+$+1) 966, 679, 637, 467, 303, 268, 224, 194, 119, 1051 91, 73, 59 and 43; HRMS (m/z) calculated for $C_{61}H_{70}N_2O_{15}S_2Si_1+H_1$=1163.4065, observed=1163.4043.

Example 14C

7-SDMS baccatin III 13-(2R,4S,5R) and (2S,4S,5R)-2,4-diphenyl-3-(9-anthracenesulfonamido)-1,3-oxazolidine-5-carboxylic acid (VII)

Following the general procedure of EXAMPLES 11A and 11B and making non-critical variations but starting with (2S,4S,5R)-2,4-diphenyl-3-(9-anthracenesulfonamido)-5-carboxy-1,3-oxazolidine (IV, EXAMPLE 13C, 185 mg, 0.36 mmol) and 7-SDMSBac(III) (93 mg, 0.13 mmol), the title compound is obtained, NMR (300 MHz, $CDCl_3$) 8.99, 8.29, 7.93, 7.72, 7.48, 7.36–7.29, 7.07, 6.99–6.93, 6.85, 6.48, 6.38, 6.19, 5.80, 5.50, 4.80, 4.73, 4.31, 4.13, 4.02, 3.73 and 3.46 δ; CMR (500 MHz, $CDCl_3$) 202.7, 170.8, 170.3, 170.0, 167.9, 139.1, 138.3, 136.4, 134.5, 132.2, 131.6, 130.9, 130.1, 130.0, 129.8, 129.5, 129.2, 129.0, 128.5, 128.3, 128.2, 126.0, 85.1, 83.4, 81.6, 80.0, 75.8, 73.0, 72.8, 65.7, 59.3, 50.1, 47.6, 44.2, 34.7, 29.2, 29.1, 28.8, 27.4, 26.4, 25.8, 23.9, 22.6, 22.0, 21.8, 21.0, 20.8, 11.0, 9.7, 0.0 and −2.2 δ; MS (m/z) 1206 ($M^+$+1), 966, 464, 346, 296, 268, 241, 224, 209, 193, 177, 121, 105, 91, 73, 59 and 43; HRMS (m/z) calculated $C_{68}H_{75}N_1O_{15}S_1Si_1+H_1$=1206.4705, observed=1206.4681.

Example 15A

7-SDMS baccatin III 13-(2R,3S)-3-amino-3-phenyl-2-hydroxypropionate (VIII)

THF (13.5 ml) and DMF (1.5 ml) are cooled to −35° and degased by alternating reduced pressure and nitrogen three times. Thiophenol (0.22 ml, 2.14 mmol) is added followed by potassium butoxide/THF (1.978 M, 0.7 ml, 1.38 mmol). After 5 minutes, 7-SDMS baccatin III 13-(2R,4S,5R)- and (2S,4S,5R)-2,4-diphenyl-3-(4-nitrobenzenesulfonamido)-1,3-oxazolidine-5-carboxylic acid ester (VII, EXAMPLE 14A, 877 mg, 0.762 mmol) is added. After the solids are added, the reaction mixture is slowly warmed to −10°. The mixture is stirred at −10° until the red color fades to yellow. After 3 hr the bath is dropped allowing the mixture to warm to 20–25°. At 20–25° the reaction is stirred for 1 hr before assaying by TLC and HPLC. Sodium bisulfite (241 mg, 2.31 mmol) is added in water (5 ml). The mixture is stirred at 20–25° and after approximately 115 hr the reaction is complete (by TLC) giving the free amine title compound, $R_f$=0.10 (ethyl acetate/cyclohexanes, 75/25).

Example 15B

7-SDMS baccatin III 13-(2R,3S)-3-amino-3-phenyl-2-hydroxypropionate (VIII)

A solution of 7-SDMS baccatin III 13-(2R,4S,5R)- and (2S,4S,5R)-2,4-diphenyl-3-benzothiazolesulfonamide-1,3- oxzalidine-5-carboxylic acid ester (VII, EXAMPLE 14B, 80 mg, 0.069 mmol) in DMF (1.5 ml) is degassed under house vacuum for 30 mins with stirring. To this mixture is added thiophenol (32 μl, 0.3 mmol) and Hunigs base (87 μl, 0.5 mmol). The mixture is stirred under a $N_2$ atmosphere at 50–55° for 12 hr. The reaction mixture is quenched with water (10 ml) and extracted with ethyl acetate (25 ml). The organic phase is back washed with water (5 ml×3) and then treated with hydrochloric acid (5%, 3 ml). The resulting organic solution is washed again with water (5 ml) and dried over magnesium sulfate. After filtering and concentrating under reduced pressure (with heat) to dryness, the residue is purified by column chromatography (silica gel; methanol/dichloromethane (1–5%)) to give the title compound, NMR (300 MHz, $CDCl_3$) 7.98, 7.54, 7.41, 7.30, 7.18, 6.32, 6.03, 5.56, 4.82, 4.29, 4.20, 4.04, 3.70, 2.37, 2.15, 2.08, 1.95, 1.72, 1.59, 1.12, 0.83–0.69 and 0.015 δ; CMR (300 MHz, $CDCl_3$) 202.5, 173.7, 171.0, 170.0, 167.8, 142.3, 141.0, 134.5, 130.9, 130.1, 129.5, 129.4, 128.9, 127.7, 85.0, 81.8, 79.6, 76.5, 75.9, 75.6, 73.1, 72.0, 59.3, 59.1, 47.5, 44.0, 38.3, 36.0, 29.1, 29.0, 28.7, 28.3, 27.4, 23.8, 23.6, 23.3, 21.7, 20.9, 20.8, 15.3, 10.9, 9.6, 0.0 and −2.4 δ; MS (m/z) 878 ($M^+$+1) 698, 697, 638, 637, 343, 213, 182, 165, 149, 136, 119, 106, 105, 91, 73, 59 and 43; HRMS (m/z) calculated $C_{47}H_{63}N_1O_{13}Si_1+H_1$=878.4147, observed=878.4140.

Example 15C

7-SDMS baccatin III 13-(2R,3S)-3-amino-3-phenyl-2-hydroxypropionate (VIII)

Following the general procedure of EXAMPLEs 15A and 15B and making non-critical variations, but starting with 7-SDMS baccatin III 13-(2R,4S,5R)- and (2S,4S,5R)-2,4-diphenyl-3-(9-anthracenesulfonamido)-1,3-oxazolidine-5-carboxylic acid (VII, EXAMPLE 14C, 30 mg, 0.03 mmol), the title compound is obtained, NMR (300 MHz, $CDCl_3$) 7.98, 7.54, 7.41, 7.30, 7.18, 6.32, 6.03, 5.56, 4.82, 4.29, 4.20, 4.04, 3.70, 2.37, 2.15, 2.08, 1.95, 1.72, 1.59, 1.12, 0.83–0.69 and 0.015 δ; CMR (300 MHz, $CDCl_3$) 202.5, 173.7, 171.0, 170.0, 167.8, 142.3, 141.0, 134.5, 130.9, 130.1, 129.5, 129.4, 128.9, 127.7, 85.0, 81.8, 79.6, 76.5, 75.9, 75.6, 73.1, 72.0, 59.3, 59.1, 47.5, 44.0, 38.3, 36.0, 29.1, 29.0, 28.7, 28.3, 27.4, 23.8, 23.6, 23.3, 21.7, 20.9, 20.8, 15.3, 10.9, 9.6, 0.0 and −2.4 δ; MS (m/z) 878 ($M^+$+1), 698, 697, 638, 637, 343, 213, 182, 165, 149, 136, 119, 106, 105, 91, 73, 59 and 43; HRMS (m/z) calculated $C_{47}H_{63}N_1O_{13}Si_1+H_1$=878.4147, observed=878.4140.

Example 15A(H)

7-SDMS baccatin III 13-(2R,3S)-3-amino-3-phenyl-2-hydroxypropionate (VIII)

THF (12.6 ml) and DMF (1.4 ml) are mixed and cooled to −350. The solvents are degased by alternating reduced pressure and nitrogen three times. Thiophenol (0.22 ml, 2.14 mmol) is added followed by potassium t-butoxide/TH (1.978 M, 0.7 ml, 1.38 mmol). After 5 min 7-SDMS baccatin III 13-(4S,5R)-4-phenyl-3-(4-nitrobenzenesulfonamido-1,3-oxazolidine-5-carboxylic acid ester (VII, 877 mg, 0.762 mmol). After solids are added, the mixture is slowly warmed to the reaction temperature of −10°. The mixture is stirred at −10° until the red color fades to yellow. After 1.5 hr the bath is removed and the mixture is permitted to warm to 20–25°. At 20–25° the reaction is stirred for 10 min before assaying by TLC and HPLC. At this point the cleavage is nearly complete (1.7% starting material by HPLC) but an intermediate which needs to be hydrolized is present. To the mixture is added sodium thiosulfate (744 mg, 7.15 mmol) with water (20 ml) in three equal portions. The mixture is stirred at 20–25° for 15 hrs before assaying by TLC. The mixture contains the free amine (Rf=0.10 in ethyl acetate/cyclohexanes, 5/25)).

Example 16A

7-SDMS baccatin III 13-(2R,3S)-3-benzamido-3-phenyl-2-hydroxypropionate (IX)

Sodium bicarbonate (485 mg, 5.77 mmol) and water 10 ml) are added to 7-SDMS baccatin III 13-(2R,3S)-3-amino-3-phenyl-2-hydroxypropionate (VIII, EXAMPLE 15A). The mixture is cooled to 0° and then benzoyl chloride (150 ml, 1.3 mmol) is added. After 1 hr the reaction is complete and the reaction mixture is diluted with water and extracted with ethyl acetate. The organic phases are combined and washed with water, saline and dried over magnesium sulfate. Chromatography of the crude product (silica gel column; 20% to 100% ethyl aetate gives the title compound, Rf=0.46 (ethyl acetate/cyclohexanes, 1/1).

Example 16B

7-SDMS baccatin III 13-(2R,3S)-3-benzamido-3-phenyl-2-hydroxypropionate (IX)

7-SDMS baccatin III 13-(2R,3S)-3-amino-3-phenyl-2-hydroxypropionate (VIII, EXAMPLE 15B, 12 mg, 0.014 mmol) in THF/water (1/1, 0.5 ml) is stirred at 20–25° for 5 mins. To this mixture is added sodium bicarbonate (12 mg, 0.15 mmol) and benzoyl chloride (4 μl, 0.03 mmol) and stirred at 25° for 30 mins. The resulting reaction mixture is diluted with ethyl acetate (10 ml) and washed with water (5 ml). The organic phase is dried over magnesium sulfate, filtered, the solvent removed under reduced pressure and the product is purified by column chromatography (silica gel; ethyl acetate/hexane (10–30%)) to give the title compound, NMR (300 MHz, $CDCl_3$) 8.04, 7.67, 7.52, 7.43–7.48, 7.34–7.25, 6.96, 6.30, 6.08, 5.72, 4.83, 4.70, 4.29, 4.22, 4.10, 4.04, 3.72, 3.50, 2.34, 2.28, 2.23, 2.08, 1.95, 1.82, 1.70, 1.61, 1.19–1.08, 0.83–0.69 and 0.02–0.00 δ; CMR (300 MHz, $CDCl_3$) 202.4, 173.3, 171.3, 170.0, 167.8, 167.7, 140.5, 138.8, 134.8, 134.5, 132.7, 131.0, 130.0, 129.8, 129.5, 129.1, 127.9, 85.0, 82.1, 79.5, 75.9, 75.5, 74.0, 73.2, 61.5, 59.4, 55.7 47.5, 44.0, 38.3, 36.0, 29.9, 29.1, 29.0, 28.8, 27.5, 23.8, 23.5, 21.7, 20.9, 15.1, 15.0, 10.9, 9.6, 0.0 and −2.4 δ; MS (m/z) 982 ($M^+$+1) 698, 697, 637, 372, 286, 268, 240, 210, 149, 133, 122, 106, 105, 73, 59 and 43; HRMS (m/z) calculated $C_{54}H_{67}N_1O_{14}Si_1+H_1$=982.4409, observed=982.4428.

Example 16A(H)

7-SDMS baccatin III 13-(2R,3S)-3-benzamido-3-phenyl-2-hydroxypropionate (IX)

Potassium carbonate (1.15 g, 8.32 mmol) is added to 7-SDMS baccatin III 13-(2R,3S)-3-amino-3-phenyl-2-hydroxypropionate (VIII, EXAMPLE 15A(H)). The resulting mixture is cooled to 0° and then benzoyl chloride (150 ml, 1.3 mmol) is added. After 1 hr the N-benzoyl product is produced. The reaction mixture is diluted with water and extracted with ethyl acetate. The organic phase is separated, washed with water, saline and dried over magnesium sulfate. Chromatography (silica gel column; ethyl acetate, 20% to 100% ethyl acetate) gives the title compound, Rf=0.46 (ethyl acetate/cyclohexane, 1/1).

Example 17

Taxol (X)

7-SDMS Baccatin III 13-(2R,3S)-3-benzamido-3-phenyl-2-hydroxypropionate (IX, EXAMPLE 16, 126 mg, 0.128 mmol) is dissolved in acetonitrile (2.5 ml). Triethylamine trihydrofluoride (123 mg, 0.763 mmol) is added under nitrogen and the resulting mixture is stirred at 50° until complete by HPLC. When complete, the mixture is extracted with methyl t-butylether and washed with sodium bicarbonate solution. The aquesous washes are back extracted and combined with the organic phase. The combined organic phases are washed with water and saline, dried over magnesium sulfate, filtered and concentrated to give the title compound, TLC $R_f$=0.39 (ethyl acetate/cyclohexane, 75/25).

Example 18

(4S,5R)-4-Phenyl-3-(4-nitrobenzenesulfonamido)-5-methoxycarbonyl-1,3-oxazolidine (III)

Methyl (2R,3S)-phenylisoserinate (I, 7.97 g, 40.8 mmole) is disolved in THF (100 ml) and treated with aqueous formaldehyde (11.55 M, 3.5 ml). The THF is removed on the rotary evaporator to azeotrope out the water. This is repeated with an additional 75 ml of THF. Toluene is then added (about 100 ml) and this also removed under reduced presure. Pyridine (50 ml) is then added and the majority removed. Pyridine (40 ml) is then added and the mixture cooled to −13°. 4-nitrophenylsulfonylchloride (9.5 g, 43.0 mmol) is then added which resultes in a temperature rise to −2°. The reaction mixture is recooled and stirred for 1.5 hr and then warmed to 20–25° and stirred for 4 hr. Water (50 mL) is added slowly and then the product is isolated by filtration and dried to give the title compound, mp=160–162°.

Example 19

(4S,5R)-4-Phenyl-5-methoxycarbonyl-1,3-oxazolidine (XI)

To a mixture of methyl (2R,3S)-phenylisoserinate (I, 1.0 g) in THF (50 mL) is added aqueous formaldehyde solution (37%, 0.47 mL). The mixture becomes homogeneous after a few minutes. The THF is removed under reduced presure to azeotrope out the water. Additional THF (50 mL) is then added and the mixture is again concentrated. The concentrate is dried under reduced pressure. Both the proton and carbon NMR show the formation of two products in about a 2:1 ratio. The title compound is CMR ($CDCl_3$) 171.8, 139.3, 128.6, 127.8, 126.8, 86.7, 82.0, 68.6 and 52.3 8.

Example 20

(2S,3R)-2-Chloro-3-hydroxy-3-phenylpropionic acid (CIV)

(±) Ethyl 2-chloro-3-hydroxy-3-phenyl propionate (CII and CIII, EXAMPLE 1, 5.5 g, 24 mmol, erythro/threo=14:3) Is incubated with lipase MAP-10 (1 g) in 0.2 M pH=7.0 phosphate buffer (100 ml). The reaction mixture is stirred vigorously at 25° for 6 days. The conversion is monitored by HPLC (nucleosil c-18 column, acetonitrile/water, 30/70, flow 2 ml/min and UV 207 nm) and shows (CII) and (CIII) (60–65%, retention time 10.9 mins) and (CIV) (40–35%, retention time 1.0 mins). The resulting reaction mixture is acidified with hydrochloric acid (5%, 15 ml) to pH<2 and extracted with ethyl acetate (50 ml×3). The combined organic extracts are extracted with aqueous potassium carbonate (10%, 25 ml) and then washed with water (25 ml×2). The organic phase is dried over magnesium sulfate and concentrated under reduced pressure to give the remaining three isomers. The combined aqueous solution is washed with ether (30 ml) and acidified with hydrochloric acid (10%, 50 ml) to pH<2. The acidic mixture is extracted with ethyl acetate (50 ml×2). The organic phase is dried over magnesium sulfate and concentrated under reduced pressure to give the crude product. An analytical sample is prepared by recrystallization. The crude acid (6.7 g, mp=76–80°) is dissolved in hot chloroform (35 ml). To this mixture heptane (10 ml) is added. The resulting mixture is cooled to 0° for 1 hr and filtered to give the title compound, mp=98–100°; $[\alpha]^{25}_D$=+1.95° (c=1.48, methanol) and −3.9° (c=1.5, chloroform); NMR (300 MHz, $CDCl_3$) 7.42–7.39, 5.28 and 4.58 δ; MS (m/z) 200 (M+), 165, 147, 129, 119, 107, 91, 79, 65 and 51; HRMS calculated for $C_9H_9O_3Cl$=200.0240, observed=200.0240.

CHART A

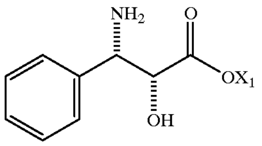

(I)

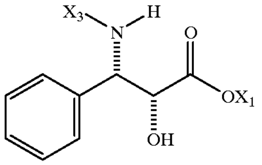

(II)

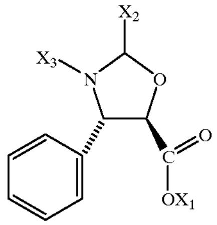

(III)

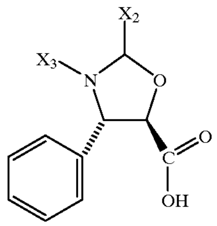

(IV)

CHART B
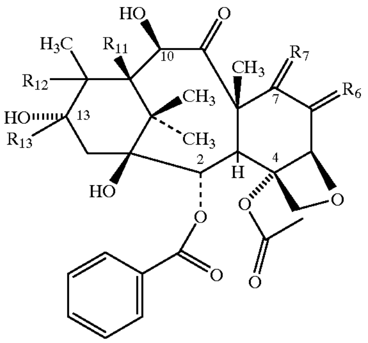
(V)
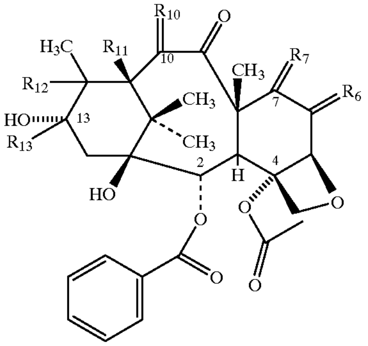
(VI)
CHART C
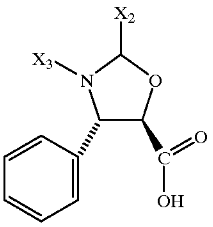
(IV)
+
(VI)
-continued
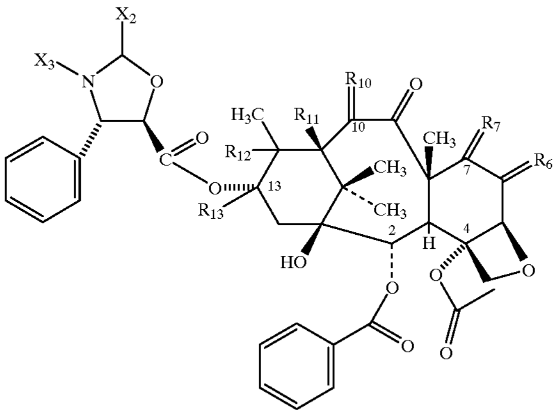
(VII)
CHART D
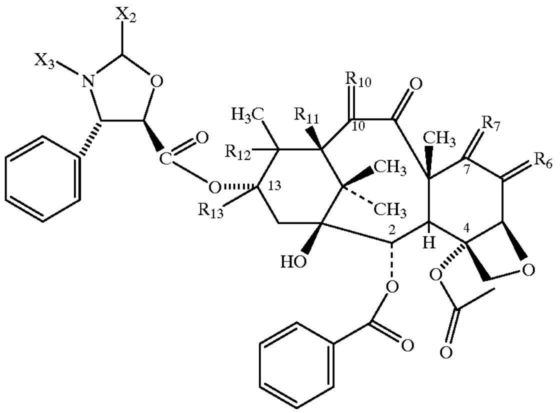
(VII)
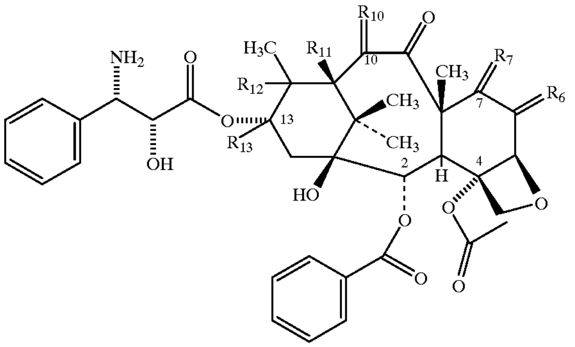
(VIII)

-continued
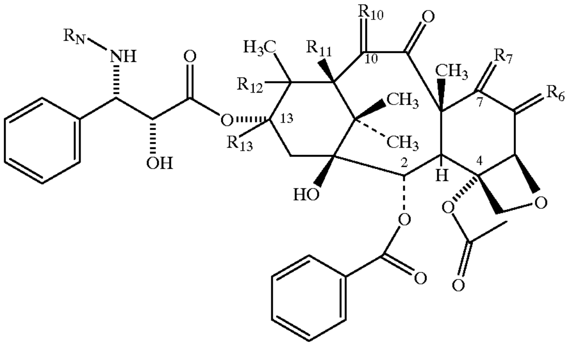
(IX)
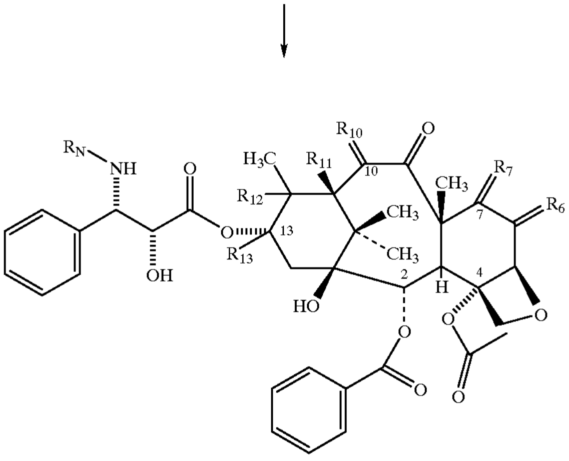
(X)
CHART E
(XI)
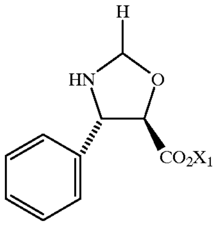
CHART F
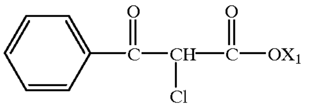
(CI)
-continued
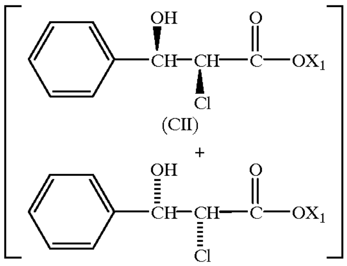
(CII)
+
(CIII)
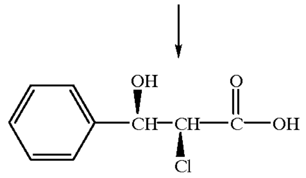
(CIV)
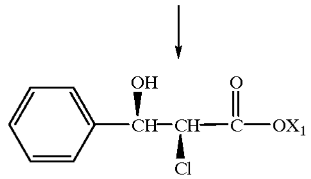
(CV)
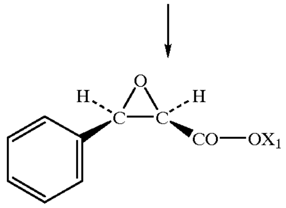
(CVI)
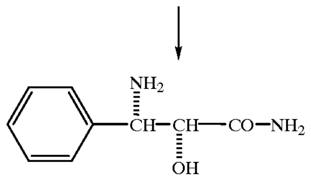
(CVII)
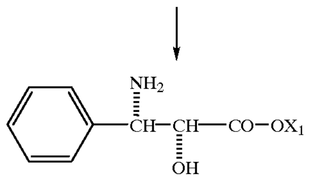
(I)
CHART G
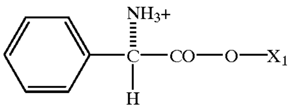
(CCI)

-continued

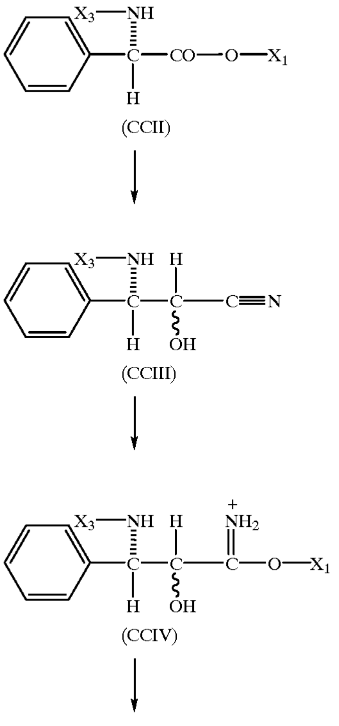

(CCII)

(CCIII)

(CCIV)

(II)

What is claimed is:

1. Phenylisoserine ester of silylated baccatin III (VII)

(VIII)

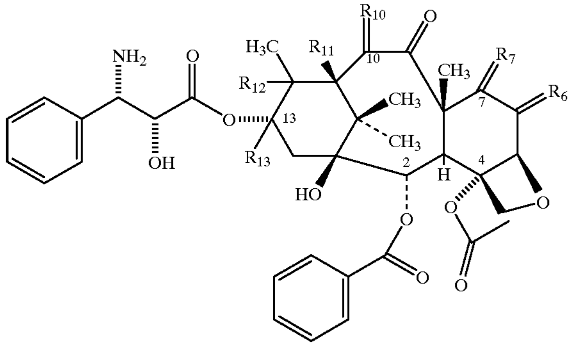

where $R_6$ and $R_7$ are:

(1) $R_6$ is —H:—H and $R_7$ is α=—H:β-$OR_{7-1}$ where $R_{7-1}$ is —$Si(R_{7-2})_3$ where two of $R_{7-2}$ are $C_1$ alkyl and the other is —$CH(CH_3)$—$CH(CH_3)_2$ and where $R_{10}$ is:

(1) α-H:β-O—CO—$CH_3$ or (2) α-H:β-O—CO—O—$CH_2$—$CCl_3$;

where $R_{11}$, $R_{12}$ and $R_{13}$ are:

(1) $R_{11}$ and $R_{12}$ are taken together to form a second bond between the carbon atoms to which they are attached and $R_{13}$ is —H.

* * * * *